United States Patent
Anand

(10) Patent No.: US 10,137,244 B2
(45) Date of Patent: Nov. 27, 2018

(54) MICROFLUIDIC DRUG DELIVERY DEVICES WITH VENTURI EFFECT

(75) Inventor: P J Anand, Ayer, MA (US)

(73) Assignee: ALCYONE LIFESCIENCES, INC., Lowell, MA (US)

( * ) Notice: Subject to any disclaimer, the term of this patent is extended or adjusted under 35 U.S.C. 154(b) by 196 days.

(21) Appl. No.: 13/563,786

(22) Filed: Aug. 1, 2012

(65) Prior Publication Data

US 2013/0035574 A1 Feb. 7, 2013

Related U.S. Application Data

(60) Provisional application No. 61/615,939, filed on Mar. 27, 2012, provisional application No. 61/513,948, (Continued)

(51) Int. Cl.
*A61M 25/00* (2006.01)
*A61M 5/168* (2006.01)
(Continued)

(52) U.S. Cl.
CPC .... *A61M 5/16804* (2013.01); *A61M 25/0023* (2013.01); *A61B 5/036* (2013.01); (Continued)

(58) Field of Classification Search
CPC .... A61M 2037/0023; A61M 2037/003; A61M 2210/0693; A61M 37/0015; A61M 5/1408; A61M 2025/0042
(Continued)

(56) References Cited

U.S. PATENT DOCUMENTS 3,460,537 A   8/1969 Zeis
3,886,948 A   6/1975 Hakim
(Continued)

FOREIGN PATENT DOCUMENTS

CN   101123919 A   2/2008
CN   101657189 A   2/2010
(Continued)

OTHER PUBLICATIONS

Burmeister et al.; Improved Ceramic-Based Multisite Microelectrode for Rapid Measurements of L-Giutamate in the CNS; Journal of Neuroscience Methods 119 (2002) 163-171; Elsevier Science B.V.
(Continued)

*Primary Examiner* — Bhisma Mehta
*Assistant Examiner* — Matthew A Engel
(74) *Attorney, Agent, or Firm* — Nutter McClennen & Fish LLP

(57) ABSTRACT

The methods, systems, and devices disclosed herein generally involve convection-enhanced delivery of drugs to a target region within a patient. Microfluidic catheter devices are disclosed that are particularly suitable for targeted delivery of drugs via convection, including devices capable of multi-directional drug delivery, devices that control fluid pressure and velocity using the venturi effect, and devices that include conformable balloons. Methods of treating various diseases using such devices are also disclosed, including methods of treating cerebral and spinal cavernous malformations, cavernomas, and hemangiomas, methods of treating neurological diseases, methods of treatment using multiple microfluidic delivery devices, methods of treating hearing disorders, methods of spinal drug delivery using microfluidic devices, and methods of delivering stem cells and therapeutics during fetal surgery. Methods of manufacturing such devices are also disclosed.

15 Claims, 29 Drawing Sheets

Related U.S. Application Data filed on Aug. 1, 2011, provisional application No. 61/513,939, filed on Aug. 1, 2011, provisional application No. 61/513,954, filed on Aug. 1, 2011, provisional application No. 61/513,961, filed on Aug. 1, 2011, provisional application No. 61/513,952, filed on Aug. 1, 2011, provisional application No. 61/513,943, filed on Aug. 1, 2011, provisional application No. 61/513,935, filed on Aug. 1, 2011.

(51) Int. Cl.

| | | |
|---|---|---|
| A61B 5/03 | (2006.01) | |
| A61B 5/145 | (2006.01) | |
| A61B 5/00 | (2006.01) | |
| A61M 5/172 | (2006.01) | |

(52) U.S. Cl.
CPC ......... *A61B 5/14503* (2013.01); *A61B 5/4839* (2013.01); *A61M 5/172* (2013.01); *A61M 25/0026* (2013.01); *A61M 2025/0042* (2013.01); *A61M 2205/50* (2013.01)

(58) Field of Classification Search
USPC .......................................... 604/20, 506, 507
See application file for complete search history.

(56) References Cited

U.S. PATENT DOCUMENTS

| | | | |
|---|---|---|---|
| 4,146,029 A | 3/1979 | Ellinwood, Jr. | |
| 4,692,146 A | 9/1987 | Hilger | |
| 4,885,945 A | 12/1989 | Chiodo | |
| 4,917,686 A | 4/1990 | Bayston et al. | |
| 4,979,284 A | 12/1990 | McMurtry et al. | |
| 5,088,208 A | 2/1992 | Wells et al. | |
| 5,101,548 A | 4/1992 | McMurtry et al. | |
| 5,190,046 A | 3/1993 | Shturman | |
| 5,407,431 A | 4/1995 | Botich et al. | |
| 5,415,648 A | 5/1995 | Malay et al. | |
| 5,509,910 A | 4/1996 | Lunn | |
| 5,590,657 A | 1/1997 | Cain et al. | |
| 5,620,479 A | 4/1997 | Diederich | |
| 5,624,396 A | 4/1997 | McNamara et al. | |
| 5,695,518 A | 12/1997 | Laerum | |
| 5,720,720 A | 2/1998 | Laske et al. | |
| 5,782,645 A | 7/1998 | Stobie et al. | |
| 5,843,150 A | 12/1998 | Dreessen et al. | |
| 5,868,711 A | 2/1999 | Kramer et al. | |
| 5,954,687 A | 9/1999 | Baudino | |
| 5,963,367 A | 10/1999 | Aksyuk et al. | |
| 6,176,842 B1 | 1/2001 | Tachibana et al. | |
| 6,193,963 B1 | 2/2001 | Stern et al. | |
| 6,224,566 B1 | 5/2001 | Loeb | |
| 6,309,634 B1 | 10/2001 | Bankiewicz et al. | |
| 6,454,945 B1 | 9/2002 | Weigl et al. | |
| 6,464,662 B1 | 10/2002 | Raghavan et al. | |
| 6,464,687 B1 | 10/2002 | Ishikawa et al. | |
| 6,471,993 B1 | 10/2002 | Shastri et al. | |
| 6,547,779 B2 | 4/2003 | Levine et al. | |
| 6,599,274 B1* | 7/2003 | Kucharczyk et al. | 604/264 |
| 6,610,235 B1 | 8/2003 | Lebouitz et al. | |
| 6,626,902 B1* | 9/2003 | Kucharczyk et al. | 606/41 |
| 6,706,009 B2 | 3/2004 | Diermann et al. | |
| 6,803,568 B2 | 10/2004 | Bousse et al. | |
| 6,953,575 B2 | 10/2005 | Bankiewicz et al. | |
| 7,029,697 B2 | 4/2006 | Segura et al. | |
| 7,048,716 B1 | 5/2006 | Kucharczyk et al. | |
| 7,316,676 B2 | 1/2008 | Peyman et al. | |
| 7,534,613 B2 | 5/2009 | Bankiewicz et al. | |
| 7,549,989 B2 | 6/2009 | Morgan et al. | |
| 7,588,574 B2 | 9/2009 | Assell et al. | |
| 7,690,325 B2 | 4/2010 | Henderson et al. | |
| 7,713,269 B2 | 5/2010 | Auge, II et al. | |
| 7,771,387 B2 | 8/2010 | Porter | |
| 7,842,006 B2 | 11/2010 | Wang et al. | |
| 7,984,929 B2 | 7/2011 | Gill | |
| 8,128,600 B2 | 3/2012 | Gill | |
| 8,192,366 B2 | 6/2012 | Mauge et al. | |
| 8,282,566 B2 | 10/2012 | Mauge et al. | |
| 8,309,355 B2 | 11/2012 | Bankiewicz et al. | |
| 8,347,696 B2 | 1/2013 | Espinosa et al. | |
| 8,539,905 B2 | 9/2013 | Cady et al. | |
| 8,602,644 B2 | 12/2013 | Choi | |
| 8,790,317 B2 | 7/2014 | Olbricht et al. | |
| 8,814,853 B2 | 8/2014 | Bosel | |
| 8,992,458 B2 | 3/2015 | Singh et al. | |
| 9,255,245 B2 | 2/2016 | Bernick et al. | |
| 9,445,838 B2 | 9/2016 | Wei et al. | |
| 9,844,585 B2 | 12/2017 | Olbricht et al. | |
| 9,919,129 B2 | 3/2018 | Singh et al. | |
| 2001/0005552 A1 | 6/2001 | Berg et al. | |
| 2002/0055702 A1 | 5/2002 | Atala et al. | |
| 2002/0055731 A1 | 5/2002 | Atala et al. | |
| 2002/0099356 A1 | 7/2002 | Unger et al. | |
| 2002/0138036 A1 | 9/2002 | Babaev | |
| 2002/0193817 A1* | 12/2002 | Lal et al. | 606/169 |
| 2003/0009153 A1 | 1/2003 | Brisken et al. | |
| 2003/0048969 A1 | 3/2003 | Hunter et al. | |
| 2003/0093032 A1 | 5/2003 | Py et al. | |
| 2003/0138403 A1 | 7/2003 | Drustrup | |
| 2003/0148539 A1 | 8/2003 | van Dam et al. | |
| 2003/0205947 A1 | 11/2003 | Klee et al. | |
| 2003/0216685 A1 | 11/2003 | Porter | |
| 2003/0216714 A1 | 11/2003 | Gill | |
| 2004/0073114 A1 | 4/2004 | Oliver et al. | |
| 2004/0176732 A1 | 9/2004 | Frazier et al. | |
| 2004/0186384 A1 | 9/2004 | Babaev | |
| 2004/0220543 A1 | 11/2004 | Heruth et al. | |
| 2004/0260241 A1 | 12/2004 | Yamamoto et al. | |
| 2005/0035983 A1 | 2/2005 | Cruchon-Dupeyrat et al. | |
| 2005/0125007 A1 | 6/2005 | Gill | |
| 2005/0137134 A1 | 6/2005 | Gill et al. | |
| 2005/0137531 A1 | 6/2005 | Prausnitz et al. | |
| 2005/0143790 A1* | 6/2005 | Kipke | A61B 5/04001 607/60 |
| 2005/0154297 A1 | 7/2005 | Gill | |
| 2005/0190999 A1 | 9/2005 | Hunter et al. | |
| 2005/0236566 A1* | 10/2005 | Liu | 250/306 |
| 2005/0269251 A1 | 12/2005 | Cork et al. | |
| 2005/0277862 A1 | 12/2005 | Anand | |
| 2006/0003310 A1 | 1/2006 | Klauke et al. | |
| 2006/0025752 A1 | 2/2006 | Broaddus et al. | |
| 2006/0122677 A1 | 6/2006 | Vardiman | |
| 2006/0135945 A1 | 6/2006 | Bankiewicz et al. | |
| 2006/0211944 A1 | 9/2006 | Mauge et al. | |
| 2006/0211945 A1 | 9/2006 | Mauge et al. | |
| 2006/0211946 A1 | 9/2006 | Mauge et al. | |
| 2007/0005017 A1 | 1/2007 | Alchas et al. | |
| 2007/0016041 A1 | 1/2007 | Nita | |
| 2007/0055180 A1 | 3/2007 | Deem et al. | |
| 2007/0088295 A1 | 4/2007 | Bankiewicz | |
| 2007/0123843 A1 | 5/2007 | Gill | |
| 2007/0128083 A1 | 6/2007 | Yantz et al. | |
| 2007/0163137 A1 | 7/2007 | Hunter et al. | |
| 2007/0191767 A1 | 8/2007 | Hennessy et al. | |
| 2007/0250054 A1 | 10/2007 | Drake | |
| 2007/0276340 A1 | 11/2007 | Poston et al. | |
| 2008/0004572 A1 | 1/2008 | Morris et al. | |
| 2008/0091104 A1* | 4/2008 | Abraham | 600/439 |
| 2008/0275466 A1 | 11/2008 | Skakoon | |
| 2008/0294096 A1 | 11/2008 | Uber, III et al. | |
| 2008/0302960 A1 | 12/2008 | Meister et al. | |
| 2009/0030373 A1 | 1/2009 | Gill | |
| 2009/0048508 A1 | 2/2009 | Gill et al. | |
| 2009/0071833 A1 | 3/2009 | Gorfinkel et al. | |
| 2009/0088730 A1 | 4/2009 | Hoofnagle et al. | |
| 2009/0112278 A1 | 4/2009 | Wingeier et al. | |
| 2009/0124976 A1 | 5/2009 | Mittermeyer | |
| 2009/0143659 A1 | 6/2009 | Li et al. | |
| 2009/0143764 A1 | 6/2009 | Nelson | |
| 2009/0198218 A1 | 8/2009 | Gill et al. | |
| 2009/0224529 A1 | 9/2009 | Gill | |
| 2009/0279815 A1 | 11/2009 | Hunter et al. | |

(56) References Cited

U.S. PATENT DOCUMENTS

| | | |
|---|---|---|
| 2009/0304314 A1 | 12/2009 | Derrick et al. |
| 2010/0030102 A1 | 2/2010 | Poston et al. |
| 2010/0030148 A1 | 2/2010 | Alchas et al. |
| 2010/0042070 A1 | 2/2010 | Gill et al. |
| 2010/0042098 A1 | 2/2010 | Cross et al. |
| 2010/0098767 A1* | 4/2010 | Olbricht et al. ............ 424/489 |
| 2010/0121307 A1 | 5/2010 | Lockard et al. |
| 2010/0130884 A1 | 5/2010 | Linninger |
| 2010/0145304 A1* | 6/2010 | Cressman ............ A61B 18/06 604/506 |
| 2010/0168583 A1 | 7/2010 | Dausch et al. |
| 2010/0185179 A1* | 7/2010 | Chan ............................ 604/508 |
| 2010/0199788 A1 | 8/2010 | Ayliffe et al. |
| 2010/0217196 A1 | 8/2010 | Nelson |
| 2010/0217228 A1 | 8/2010 | Grahn et al. |
| 2010/0217236 A1 | 8/2010 | Gill et al. |
| 2010/0256549 A1 | 10/2010 | Kralick et al. |
| 2010/0298163 A1 | 11/2010 | Juncker et al. |
| 2010/0312193 A1 | 12/2010 | Stratton et al. |
| 2010/0318061 A1 | 12/2010 | Derrick et al. |
| 2010/0318064 A1 | 12/2010 | Derrick et al. |
| 2010/0324127 A1 | 12/2010 | Kay |
| 2011/0003330 A1 | 1/2011 | Durack |
| 2011/0009879 A1 | 1/2011 | Derrick et al. |
| 2011/0098580 A1 | 4/2011 | Mikhail et al. |
| 2011/0106054 A1* | 5/2011 | Osborne ............ A61B 17/8816 604/518 |
| 2011/0137289 A1 | 6/2011 | Kunst |
| 2011/0178505 A1 | 7/2011 | Odland et al. |
| 2011/0184503 A1 | 7/2011 | Xu et al. |
| 2011/0200244 A1 | 8/2011 | Ashton et al. |
| 2011/0218494 A1 | 9/2011 | Gerrans et al. |
| 2011/0275994 A1 | 11/2011 | Iwase et al. |
| 2011/0282319 A1 | 11/2011 | Gill |
| 2011/0301235 A1 | 12/2011 | Erlanson et al. |
| 2012/0019270 A1 | 1/2012 | Amodei et al. |
| 2012/0041394 A1 | 2/2012 | Haider et al. |
| 2012/0046666 A1 | 2/2012 | Klein |
| 2012/0060847 A1 | 3/2012 | Stratton et al. |
| 2012/0065496 A1 | 3/2012 | Stratton et al. |
| 2012/0083739 A1 | 4/2012 | Nelson |
| 2012/0083742 A1 | 4/2012 | Nelson |
| 2012/0123391 A1 | 5/2012 | Gill et al. |
| 2012/0209110 A1 | 8/2012 | Bankiewicz et al. |
| 2012/0209303 A1 | 8/2012 | Frankhouser et al. |
| 2012/0257846 A1 | 10/2012 | Derrick et al. |
| 2012/0302959 A1 | 11/2012 | Fielder et al. |
| 2012/0310182 A1 | 12/2012 | Fielder et al. |
| 2012/0310215 A1 | 12/2012 | Stout et al. |
| 2013/0019488 A1 | 1/2013 | McMurtry et al. |
| 2013/0035560 A1 | 2/2013 | Anand et al. |
| 2013/0035660 A1 | 2/2013 | Anand |
| 2013/0046230 A1 | 2/2013 | Lewis, Jr. et al. |
| 2013/0072882 A1 | 3/2013 | Ogawa et al. |
| 2013/0079596 A1 | 3/2013 | Smith |
| 2013/0079779 A1 | 3/2013 | Smith |
| 2013/0204202 A1 | 8/2013 | Trombly et al. |
| 2013/0310767 A1 | 11/2013 | Solar et al. |
| 2014/0039459 A1 | 2/2014 | Folk et al. |
| 2014/0171760 A1 | 6/2014 | Singh et al. |
| 2014/0171902 A1 | 6/2014 | Singh et al. |
| 2014/0276417 A1 | 9/2014 | Nelson |
| 2014/0371711 A1 | 12/2014 | Singh et al. |
| 2014/0371712 A1 | 12/2014 | Olbricht et al. |
| 2015/0038949 A1 | 2/2015 | Singh et al. |
| 2015/0133887 A1 | 5/2015 | Singh et al. |
| 2016/0213312 A1 | 7/2016 | Singh et al. |
| 2016/0346505 A1 | 12/2016 | Gill et al. |
| 2018/0193595 A1 | 7/2018 | Singh et al. |

FOREIGN PATENT DOCUMENTS

| | | |
|---|---|---|
| EP | 2 042 212 A1 | 4/2009 |
| JP | 2009-507531 A | 2/2009 |
| JP | 2009-526589 A | 7/2009 |
| JP | 2010-501233 A | 1/2010 |
| JP | 2011-212502 A | 10/2011 |
| WO | 95/05864 A1 | 3/1995 |
| WO | 97/00442 A1 | 1/1997 |
| WO | 97/17105 A1 | 5/1997 |
| WO | 97/40874 A1 | 11/1997 |
| WO | 97/48425 A2 | 12/1997 |
| WO | 98/52064 A1 | 11/1998 |
| WO | 99/52585 A1 | 10/1999 |
| WO | 00/51669 A1 | 9/2000 |
| WO | 02/068036 A1 | 9/2002 |
| WO | 02/085431 A2 | 10/2002 |
| WO | 2004/060465 A2 | 7/2004 |
| WO | 2006/015091 A2 | 2/2006 |
| WO | 2007/093778 A1 | 8/2007 |
| WO | 2007/104953 A1 | 9/2007 |
| WO | 2007/133545 A2 | 11/2007 |
| WO | 2008100930 A2 | 8/2008 |
| WO | 2008/134509 A1 | 11/2008 |
| WO | 2010/006293 A2 | 1/2010 |
| WO | 2010/081072 A2 | 7/2010 |
| WO | 2011/098769 A1 | 8/2011 |
| WO | 2011109735 A2 | 9/2011 |
| WO | 2012/145652 A1 | 10/2012 |
| WO | 2013/019830 A2 | 2/2013 |
| WO | 2014/016591 A1 | 1/2014 |

OTHER PUBLICATIONS

International Search Report for International Application No. PCT/US2011/027238, dated Nov. 16, 2011.

Saltzman et al.; Building Drug Delivery Into Tissue Engineering; Nature Reviews/Drug Discovery; 2002 Macmillan Magazines Ltd.; vol. 1; Mar. 2002; pp. 177-186.

Olbricht, William L. et al., Microfluidic Probes in the Treatment of Brain-Related Diseases, Drug News and Perspectives, 2010, 23(8)—7 pages (Oct. 2010).

International Search Report and Written Opinion for Application No. PCT/US2014/042726 dated Oct. 28, 2014 (13 Pages).

International Search Report and Written Opinion for Application No. PCT/US2013/076084 dated Mar. 11, 2014 (13 Pages).

Invitation to Pay Additonal Fees for Application No. PCT/US2014/049031, dated Nov. 24, 2014 (2 pages).

International Search Report and Written Opinion for Application No. PCT/2014/049031 dated Jan. 30, 2015 (16 pages).

Lewis et al., Design and characterization of a high-power ultrasound driver with ultralow-output impedance. Rev Sci Instrum. Nov. 2009:80(11):114704.1-114704.8.

International Search Report and Written Opinion for Application No. PCT/US2012/049100, dated Jan. 29, 2013. (12 pages).

Debinski, W., et al., "Convection-enhanced Delivery for the Treatment of Brain Tumors," Expert Rev Neurother. Oct. 2009; 9(10): 1519-1527.

Fiandaca, M., et al., "Use of Convection-Enhanced Delivery with Liposomal Toxins in Neurooncology," Toxins 2011, 3(4), 369-397.

Chinese Office Action for Application No. 201280046268.8, dated May 27, 2015 (45 pages).

Extended European Search Report for Application No. 12819276.2, dated Mar. 23, 2015 (7 pages).

Rapoport, S.I., "Osmotic opening of the blood-brain barrier: principles, mechanism, and therapeutic applications," Cell. Mol. Neurobiol. 20: 217-30 (2000).

Extended European Search Report for Application No. 148143803, dated Nov. 11, 2016. (7 pages).

Extended European Search Report for Application No. 14831460.2, dated Mar. 2, 2017 (7 pages).

Japanese Office Action for Application No. 2015-549618, dated Sep. 5, 2017 (12 pages).

Extended European Search Report for Application No. 13865917.2, dated Aug. 17, 2016 (6 pages).

(56) References Cited

OTHER PUBLICATIONS

Japanese Office Action for Application No. 2016-531883, dated Jun. 5, 2018 (10 pages).

\* cited by examiner

MICROFLUIDIC DRUG DELIVERY DEVICES WITH VENTURI EFFECT

CROSS-REFERENCE TO RELATED APPLICATIONS

This application claims priority to U.S. Provisional Application No. 61/513,935 filed on Aug. 1, 2011, U.S. Provisional Application No. 61/513,939 filed on Aug. 1, 2011, U.S. Provisional Application No. 61/513,943 filed on Aug. 1, 2011, U.S. Provisional Application No. 61/513,948 filed on Aug. 1, 2011, U.S. Provisional Application No. 61/513,952 filed on Aug. 1, 2011, U.S. Provisional Application No. 61/513,954 filed on Aug. 1, 2011, U.S. Provisional Application No. 61/513,961 filed on Aug. 1, 2011, and U.S. Provisional Application No. 61/615,939 filed on Mar. 27, 2012, which are each hereby incorporated by reference in their entirety.

FIELD

The present invention relates to methods for treatment of human and veterinary diseases and devices for delivery of therapeutics as well as to devices to provide diagnostic data via aspiration to stratify treatment and trials. In particular, the present invention relates to microfluidic drug delivery devices and associated treatment methods.

BACKGROUND

In convection-enhanced delivery (CED), drugs are infused locally into tissue through a cannula inserted into the tissue. Transport of the infused material is dominated by convection, which enhances drug penetration into a target tissue compared with diffusion-mediated delivery or systemic delivery.

CED has emerged as a leading investigational delivery technique for the treatment of several disorders. For example, one of the fundamental barriers to treatment of chronic neuropathological conditions is the Blood-Brain-Barrier (BBB). The BBB protects the brain by very selectively allowing only molecules of very small size and that are soluble in fat. Larger molecule drugs that have the potential to cure patients with neurological disorders cannot cross the BBB. Direct targeted intraparenchymal injection and/or via CED can be used to bypass the blood-brain barrier by infusing compounds through a needle, cannula, or microcatheter directly into brain parenchyma or a brain tumor. Clinical trials using existing devices show mixed results and suggest that the outcome of the therapy depends strongly on the extent of penetration and distribution of the drug into the brain, which is determined by infusion velocity, the relative rates of convection and elimination during CED, and various properties of the target tissue.

To increase the infusion velocity, flexible microcatheter designs have been constructed to reduce backflow of the drug-containing fluid between the tissue and needle-shaft interface. To reduce the elimination rate and thereby extend the penetration distance, infused compounds have been incorporated into nanoparticles such as liposomes or polymeric beads, which protect the compounds during transport. However, backflow of drug during CED treatment still remains a critical problem in clinical practice and the transport of nanoparticles through the brain is hindered, because the size of the nanoparticles is comparable to the size of a typical "pore" of the extracellular space. In addition, the poroelastic nature of the brain tissue contributes to backflow or reflux. Furthermore, it can be difficult to control the spatial distribution of infused molecules and nanoparticles when tissue characteristics vary within the treatment region, such as in heterogeneous tissue and near white matter tracts in the brain. There is therefore a need for improved CED devices, e.g., CED devices with increased penetration distance and/or increased control over the spatial distribution of the infused drug.

SUMMARY

The methods, systems, and devices disclosed herein generally involve convection-enhanced delivery of drugs to a target region within a patient. Microfluidic catheter devices are disclosed that are particularly suitable for targeted delivery of drugs via convection, including devices capable of multi-directional drug delivery and devices that control fluid pressure and velocity using the venturi effect. Methods of treating various diseases using such devices are also disclosed, including methods of treating cerebral and spinal cavernous malformations, cavernomas, and hemangiomas, methods of treating neurological diseases, methods of treatment using multiple microfluidic delivery devices, methods of treating hearing disorders, methods of spinal drug delivery using microfluidic devices, and methods of delivering stem cells and therapeutics during fetal surgery. Methods of manufacturing such devices are also disclosed.

Microfluidic convection-enhanced-delivery (CED) devices and methods of use are disclosed wherein the devices have an insertion support scaffold and a plurality of fluid delivery conduits extending longitudinally that are oriented to deliver a therapeutic agent in different directions. The conduits can also be used to aspirate fluid samples. In some embodiments, the conduits can be disposed on different side surfaces of the scaffold, e.g., circumferentially in a spaced-apart relationship around the side surface of the scaffold. In other embodiments, each conduit can also have a plurality of outlet ports spaced-apart from each other longitudinally and oriented to deliver therapeutic agents in different directions.

Methods of treating neurological disorders are disclosed whereby a microfluidic intraparenchymal delivery, neuro-ventricular delivery, or convection-enhanced-delivery (CED) probe is implanted into a brain of a patient (e.g., a human or animal), the probe comprising a semi-rigid or degradable scaffold and a fluid delivery conduit; and a fluid comprising at least one therapeutic agent under positive pressure is delivered through the conduit and into the brain. In various embodiments, the therapeutic agent can be a chemotherapeutic agent, an antibody, a nucleic acid construct, an RNAi agent, an antisense oligonucleotide or a gene therapy vector. In other embodiments, a cofactor such as a corticosteroid can be co-administered via the conduit with the therapeutic agent. The neurological disorders can include, without limitation, central-nervous-system (CNS) neoplasms, epilepsy, Parkinson's Disease, movement disorders, Huntington's Disease, ALS, Alzheimer's Disease, stroke, brain injury, and neurological diseases.

Methods of delivering a therapeutic agent directly to a target site within a region of the central nervous system of a patient are disclosed using a plurality of microfluidic convection-enhanced-delivery (CED) probes whereby the probes are positioned in a spaced relationship around the target site such that one or more fluid outlet ports formed in the probes are aligned with the target site; and a fluid comprising a therapeutic agent under positive pressure is supplied through one or more fluid conduits formed in each of the plurality of probes to deliver the fluid through the one or more fluid outlet ports and into the target site. For example, the target site can be a tumor and the probes are inserted through either a single or multiple openings in the skull. In another aspect of the invention, the pressure at which fluid is supplied to each of the plurality of probes can be adjusted based on feedback from a microsensor disposed within at least one of the plurality of probes.

Methods of treating balance or hearing disorders are disclosed, in which an opening is formed in a skull of a patient to access a portion of an ear of the patient, a microfluidic convection-enhanced-delivery (CED) probe is implanted into the portion of the ear, and a fluid comprising at least one therapeutic agent is delivered under positive pressure through the conduit and into the portion of the ear. In one embodiment, the probe can include a degradable scaffold and a fluid delivery conduit and the target region for therapy can be the inner ear, the cochlea, the organ of Corti or the basilar membrane. In another aspect, the therapeutic agent can be a gene therapy vector, e.g., to deliver a human atonal gene. The method can further include delivering a cofactor, such as a corticosteroid, to the portion of the ear to improve fluid delivery.

Methods of delivering a therapeutic agent to a target region within a spinal canal of a patient are disclosed in which a microfluidic convection-enhanced-delivery (CED) probe is implanted into a target area, a fluid comprising the therapeutic agent under positive pressure is delivered through the conduit and into the target region, and substantially none of the delivered fluid mixes with cerebrospinal fluid (CSF) of the patient. In one embodiment, the probe includes a degradable scaffold and a fluid delivery conduit. In another aspect, the therapeutic agent can include stem cells for the treatment of ALS.

Microfluidic convection-enhanced-delivery (CED) devices are disclosed having a substrate; a conduit layer deposited on the substrate, the conduit layer defining therein at least one fluid delivery conduit with at least one fluid outlet port and a flow restriction formed within the at least one fluid delivery conduit at or near the outlet, the flow restriction being configured to adjust a pressure of fluid being directed through the at least one fluid delivery conduit. In certain embodiments, the flow restriction includes a constricted region of the at least one fluid delivery conduit having a cross-sectional area that is less than a cross-sectional area of a proximally-adjacent portion of the at least one fluid delivery conduit, and preferably at least about 20% less than the cross-sectional area of the proximally-adjacent portion.

Methods of delivering a therapeutic agent during fetal surgery are disclosed in which a microfluidic convection-enhanced-delivery (CED) probe is implanted into a target region of a fetus or a patient in which the fetus is disposed, the probe comprising a degradable scaffold and a fluid delivery conduit. In one embodiment, the method also includes delivering fluid comprising the therapeutic agent under positive pressure through the conduit and into the target region. The target region can be or can include an umbilical cord, an umbilical artery, an umbilical vein, a placenta, and/or a uterine wall. In one embodiment, the therapeutic agent comprises stem cells.

In some embodiments, microfluidic CED devices are disclosed in which a plurality of fluid delivery conduits are provided having longitudinally staggered outlet ports. An inflatable member such as a reinforced conformable balloon can be coupled to and in fluid communication with one or more of the fluid delivery conduits. Methods of delivering a drug such as an anti-angiogenesis factor to a cavernous malformation are also disclosed herein. In some embodiments, the method can include delivering the drug to the cavernous malformation using a microfluidic CED device and then inflating an inflatable member within the cavernous malformation to compress the drug into the surrounding tissue.

A cavernous malformation (CCM) is a collection of small blood vessels (capillaries) in the central nervous system (CNS) that is enlarged and irregular in structure. In CCM, the walls of the capillaries are thinner than normal, less elastic, and prone to leaking. Cavernous malformations can occur anywhere in the body, but usually only produce symptoms when they are found in the brain and spinal cord. Some people with CCM—experts estimate 25 percent—will never experience any related medical problems. Others will have serious symptoms such as seizures (most commonly), headaches, paralysis, hearing or vision changes, and bleeding in the brain (cerebral hemorrhage).

There are no effective cures for CCM. Seizures are usually treated with antiepileptic drugs. If seizures don't respond to medication, or there is recurring bleeding in the brain, surgical removal of the lesion(s) using microsurgical techniques is sometimes necessary.

Cavernomas occur sporadically (spontaneously in a non-inherited manner) in the majority of cases, but in some cases may demonstrate inheritance (familial; i.e., a positive or strong family history of cavernous malformations). In familial cases, a specific chromosome 7 gene abnormality has been demonstrated, and familial cavernous malformation has been reported to be more common in Hispanic (especially Mexican-American) persons. In familial cases, cavernous malformations are more commonly multiple (i.e., two or more cavernomas present at the time of diagnosis), and may also involve the spinal cord.

Cavernomas may be asymptomatic, or may present with seizures (60%) or with progressive neurological impairment or "deficits" (50%). Some can present with hydrocephalus or raised intracranial pressure (headache, nausea, vomiting, visual disturbance, sleepiness) depending on their size and location. It is uncommon for cavernomas to cause sudden catastrophic or devastating neurological injury, but the progressive brain (or spinal cord) injury associated with cavernomas may be severely disabling as time goes on.

This is due at least in part to repeated bouts of hemorrhage in the cavernoma. Different cavities of the cavernoma may have different ages of blood products. The walls are fragile, and the growth of micro blood vessels into these lesions results in blood product (hemosiderin) leeching around the cavernoma, and cycles of cavernoma growth through hemorrhage and re-hemorrhage. The hemorrhage is rarely a large devastating hemorrhage.

Antiangiogenic therapy inhibits the growth of new blood vessels. Because new blood vessel growth plays a critical role in many disease conditions, including disorders that cause blindness, arthritis, and cancer, angiogenesis inhibition is a "common denominator" approach to treating these diseases. Antiangiogenic drugs exert their beneficial effects in a number of ways: by disabling the agents that activate and promote cell growth, or by directly blocking the growing blood vessel cells. Angiogenesis inhibitory properties have been discovered in more than 300 substances, ranging from molecules produced naturally in animals and plants, such as green tea extract, to new chemicals synthesized in the laboratory. A number of medicines already approved by the U.S. Food and Drug Administration (FDA) have also been found to possess antiangiogenic properties, including celecoxib (Celebrex), bortezomib (Velcade), and interferon. Many inhibitors are currently being tested in clinical trials for a variety of diseases in human patients, and some in veterinary settings.

Rapamycin (now called Sirolimus) is a drug used to keep the body from rejecting organ and bone marrow transplants. It is now known that Rapamycin blocks certain white blood cells that can reject foreign tissues and organs (antiangiogenic). It also blocks a protein that is involved in cell division. It is a type of antibiotic, a type of immunosuppressant, and a type of serine/threonine kinase inhibitor.

In one aspect of at least one embodiment of the invention, a microfluidic convection-enhanced-delivery (CED) device is provided that includes an insertion support scaffold having a proximal end and a distal end and a plurality of fluid delivery conduits extending longitudinally therethrough, each conduit having an inlet port and at least one outlet port. The plurality of conduits can be disposed near the distal end of the scaffold and oriented to deliver a therapeutic agent in different directions. The plurality of conduits can be configured to aspirate fluids.

Each of the plurality of conduits can be coupled to a respective one of a plurality of side surfaces of the scaffold and/or the plurality of conduits can be positioned in a spaced relationship about a continuous circumferential side surface of the scaffold.

The at least one outlet port can include a plurality of outlet ports spaced a distance apart from one another between proximal and distal ends of each conduit. Each of the plurality of outlet ports can have an area that is greater than an area of any outlet port positioned proximally thereto. The plurality of conduits can be formed from at least one of a parylene composition, a silastic composition, a polyurethane composition, and a PTFE composition, and/or can be disposed within a plurality of corresponding recesses formed in the scaffold.

The device can also include a fluid reservoir in fluid communication with the inlet ports of the plurality of conduits and configured to supply a fluid thereto under positive pressure. The plurality of conduits can be flexible.

At least one of the plurality of conduits can include an embedded microsensor, which can include at least one of an interrogatable sensor, a pressure sensor, a glutamate sensor, a pH sensor, a temperature sensor, an ion concentration sensor, a carbon dioxide sensor, an oxygen sensor, and a lactate sensor.

The scaffold can be rigid, semi-rigid, and/or degradable, and the distal end of the scaffold can have an atraumatic shape configured to penetrate tissue without causing trauma. The scaffold can be formed from a degradable thermoplastic polymer (e.g., a degradable thermoplastic polyester and/or a degradable thermoplastic polycarbonate). In one embodiment, the scaffold is formed from poly(lactic-co-glycolic acid) (PLGA).

The scaffold can contain a quantity of a drug, can be coated with a drug, and/or can be impregnated with at least one of an antibacterial agent and an anti-inflammatory agent. For example, the scaffold can be impregnated with a corticosteroid, such as dexamethasone.

Each of the plurality of conduits can be in fluid communication with a respective micro-capillary tube. The scaffold can include a body and an elongate distal tip, and the device can further include a nose disposed at an interface between the body and the distal tip such that the nose encapsulates a distal portion of the body.

In another aspect of at least one embodiment of the invention, a method of delivering a therapeutic agent to a brain of a patient is provided that includes forming an opening through a skull of the patient, advancing a scaffold through the opening in the skull and into the brain, and supplying a fluid comprising the therapeutic agent under positive pressure to a plurality of fluid delivery conduits, each of the plurality of conduits being coupled to a respective side surface of the scaffold. The method also includes ejecting the fluid from one or more outlet ports formed in each of the plurality of conduits to deliver the fluid to the brain in a radial pattern substantially 360 degrees around the scaffold.

The method can also include allowing the scaffold to degrade within the brain and thereby release a corticosteroid impregnated in the scaffold and/or delivering an enzyme through the plurality of conduits in unison with the fluid to enhance penetration of the therapeutic agent into the brain.

In another aspect of at least one embodiment of the invention, a method of delivering a therapeutic agent to a patient is provided. The method can include advancing a scaffold into a target region of the patient, supplying a fluid comprising the therapeutic agent under positive pressure to a plurality of fluid delivery conduits, each of the plurality of conduits being coupled to a respective side surface of the scaffold, and ejecting the fluid from one or more outlet ports formed in each of the plurality of conduits to deliver the fluid to the target region in multiple directions.

The method can include allowing the scaffold to degrade and thereby release a corticosteroid impregnated in the scaffold. The method can include delivering an enzyme through the plurality of conduits in unison with the fluid to enhance penetration of the therapeutic agent into the target region. In some embodiments, ejecting the fluid can include delivering the fluid to the target region in a radial pattern substantially 360 degrees around the scaffold. The method can be used to treat at least one condition selected from central-nervous-system (CNS) neoplasm, intractable epilepsy, Parkinson's disease, Huntington's disease, stroke, lysosomal storage disease, chronic brain injury, Alzheimer's disease, amyotrophic lateral sclerosis, balance disorders, hearing disorders, and cavernous malformations.

In another aspect of at least one embodiment of the invention, a method of treating central-nervous-system (CNS) neoplasm is provided that includes implanting a microfluidic convection-enhanced-delivery (CED) probe into a brain of a patient, the probe comprising a degradable scaffold and a fluid delivery conduit, and delivering fluid comprising at least one therapeutic agent under positive pressure through the conduit and into the brain.

The therapeutic agent can include at least one of an antibody (e.g., an anti-epidermal growth factor (EGF) receptor monoclonal antibody) and a nucleic acid construct (e.g., a ribonucleic acid interference (RNAi) agent, an antisense oligonucleotide, a viral vector, an adenovirus, and/or an adeno-associated viral vector). The method can also include delivering a cofactor to the brain to improve fluid delivery. The cofactor can include at least one of a corticosteroid impregnated in the scaffold, a corticosteroid coated onto the scaffold, and a propagation enhancing enzyme.

In another aspect of at least one embodiment of the invention, a method of treating intractable epilepsy is provided that includes implanting a microfluidic convection-enhanced-delivery (CED) probe into a brain of a patient, the probe comprising a degradable scaffold and a fluid delivery conduit, and delivering fluid comprising an anti-convulsive agent under positive pressure through the conduit and into the brain.

In another aspect of at least one embodiment of the invention, a method of treating Parkinson's disease is provided that includes implanting a microfluidic convection-enhanced-delivery (CED) probe into a brain of a patient, the probe comprising a degradable scaffold and a fluid delivery conduit, and delivering fluid comprising a protein under positive pressure through the conduit and into the brain. The protein can include glial cell-derived neurotrophic factor (GDNF) or brain-derived neurotrophic factor (BDNF) or genetic materials.

In another aspect of at least one embodiment of the invention, a method of treating Huntington's disease is provided that includes implanting a microfluidic convection-enhanced-delivery (CED) probe into a brain of a patient, the probe comprising a degradable scaffold and a fluid delivery conduit, and delivering fluid comprising a nucleic acid construct under positive pressure through the conduit and into the brain. The nucleic acid construct can include at least one of a ribonucleic acid interference (RNAi) agent and an antisense oligonucleotide.

In another aspect of at least one embodiment of the invention, a method of treating stroke is provided that includes implanting a microfluidic convection-enhanced-delivery (CED) probe into a brain of a patient, the probe comprising a degradable scaffold and a fluid delivery conduit, and delivering fluid comprising a neurotrophin under positive pressure through the conduit and into the brain.

In another aspect of at least one embodiment of the invention, a method of treating lysosomal storage disease is provided that includes implanting a microfluidic convection-enhanced-delivery (CED) probe into a brain of a patient, the probe comprising a degradable scaffold and a fluid delivery conduit, and delivering fluid comprising a protein under positive pressure through the conduit and into the brain. The protein can include lysosomal enzymes.

In another aspect of at least one embodiment of the invention, a method of treating chronic brain injury is provided that includes implanting a microfluidic convection-enhanced-delivery (CED) probe into a brain of a patient, the probe comprising a degradable scaffold and a fluid delivery conduit, and delivering fluid comprising a protein under positive pressure through the conduit and into the brain. The protein can include at least one of brain-derived neurotrophic factor (BDNF) and fibroblast growth factor (FGF).

In another aspect of at least one embodiment of the invention, a method of treating Alzheimer's disease is provided that includes implanting a microfluidic convection-enhanced-delivery (CED) probe into a brain of a patient, the probe comprising a degradable scaffold and a fluid delivery conduit, and delivering fluid comprising at least one of anti-amyloids and nerve growth factor (NGF), or genes or vectors, under positive pressure through the conduit and into the brain.

In another aspect of at least one embodiment of the invention, a method of treating amyotrophic lateral sclerosis is provided that includes implanting a microfluidic convection-enhanced-delivery (CED) probe into a brain of a patient, the probe comprising a degradable scaffold and a fluid delivery conduit, and delivering fluid comprising a protein under positive pressure through the conduit and into the brain. The protein can include at least one of brain-derived neurotrophic factor (BDNF) and ciliary neurotrophic factor (CNTF).

In another aspect of at least one embodiment of the invention, a method of delivering a therapeutic agent to a target region within a spinal canal of a patient is provided that includes implanting a microfluidic convection-enhanced-delivery (CED) probe into the target area, the probe comprising a degradable scaffold and a fluid delivery conduit, and delivering fluid comprising the therapeutic agent under positive pressure through the conduit and into the target region. In one embodiment, substantially none of the fluid mixes with cerebrospinal fluid (CSF) of the patient. The therapeutic agent can include stem cells for the treatment of ALS In another aspect of at least one embodiment of the invention, a method of delivering a therapeutic agent to a target site within a brain of a patient using a plurality of microfluidic convection-enhanced-delivery (CED) probes is provided. The method includes positioning the plurality of probes in a spaced relationship around the target site such that one or more fluid outlet ports formed in each of the plurality of probes are aligned with the target site. The method also includes supplying a fluid comprising the therapeutic agent under positive pressure through one or more fluid conduits formed in each of the plurality of probes to deliver the fluid through the one or more fluid outlet ports and into the target site.

In one embodiment, the target site can include a tumor. The plurality of probes can be inserted through a single opening in the skull or can be inserted through separate openings in the skull. The method can also include adjusting a respective pressure at which fluid is supplied to each of the plurality of probes based on feedback from a microsensor disposed within at least one of the plurality of probes. The microsensor can include at least one of an interrogatable sensor, a pressure sensor, a glutamate sensor, a pH sensor, a temperature sensor, an ion concentration sensor, a carbon dioxide sensor, an oxygen sensor, and a lactate sensor.

In another aspect of at least one embodiment of the invention, a microfluidic convection-enhanced-delivery (CED) device is provided that includes a substrate, a conduit layer deposited on the substrate, the conduit layer having formed therein at least one fluid delivery conduit having a proximal end, a distal end, a fluid inlet port, and at least one fluid outlet port, and a flow restriction formed within the at least one fluid delivery conduit at or near the distal end thereof, the flow restriction being configured to adjust a pressure of fluid being directed through the at least one fluid delivery conduit.

The device can also include an insertion support scaffold to which the substrate is coupled. The substrate can be formed from silicon and the conduit layer can be formed from parylene. In one embodiment, the flow restriction includes a constricted region of the at least one fluid delivery conduit having a cross-sectional area that is less than a cross-sectional area of a proximally-adjacent portion of the at least one fluid delivery conduit.

The cross-sectional area of the constricted region can be approximately 20% less, approximately 30% less, or approximately 40% less than the cross-sectional area of the proximally-adjacent portion.

In one embodiment, the proximally-adjacent portion has a height between about 1 micron and about 50 microns and the constricted region has a height between about 1 micron and about 25 microns. In another embodiment, the proximally-adjacent portion has a width between about 10 microns and about 100 microns and the constricted region has a width between about 5 microns and about 50 microns.

The at least one fluid outlet port can include a plurality of outlet ports spaced a distance apart from one another between proximal and distal ends of the at least one fluid delivery conduit. Each of the plurality of outlet ports can have an area that is greater than an area of any outlet port positioned proximally thereto. The at least one fluid delivery conduit can be formed from at least one of a parylene composition, a silastic composition, a polyurethane composition, and a PTFE composition. The device can also include a fluid reservoir in fluid communication with the fluid inlet ports of the at least one fluid delivery conduit and configured to supply a fluid thereto under positive pressure. The at least one fluid delivery conduit can include an embedded microsensor. The embedded microsensor can include at least one of an interrogatable sensor, a pressure sensor, a glutamate sensor, a pH sensor, a temperature sensor, an ion concentration sensor, a carbon dioxide sensor, an oxygen sensor, and a lactate sensor. The at least one fluid delivery conduit can be configured to aspirate fluids.

In another aspect of at least one embodiment of the invention, a method of delivering a therapeutic agent to a patient is provided. The method can include advancing a substrate to a target region of the patient, the substrate having at least one fluid delivery conduit, the at least one fluid delivery conduit including a flow restriction formed at or near a distal end thereof configured to adjust a pressure of fluid being directed through the at least one fluid delivery conduit. The method can also include supplying a fluid comprising the therapeutic agent under positive pressure to the at least one fluid delivery conduit. The method can also include ejecting the fluid from one or more outlet ports formed in the at least one fluid delivery conduit to deliver the fluid to the target region. The method can also include delivering an enzyme through the at least one fluid delivery conduit in unison with the fluid to enhance penetration of the therapeutic agent into the target region. In some embodiments, the method can be used to treat at least one condition selected from central-nervous-system (CNS) neoplasm, intractable epilepsy, Parkinson's disease, Huntington's disease, stroke, lysosomal storage disease, chronic brain injury, Alzheimer's disease, amyotrophic lateral sclerosis, balance disorders, hearing disorders, and cavernous malformations.

In another aspect of at least one embodiment of the invention, a method of treating balance or hearing disorders is provided that includes forming an opening in a skull of a patient to access a portion of an ear of the patient and implanting a microfluidic convection-enhanced-delivery (CED) probe into the portion of the ear, the probe comprising a degradable scaffold and a fluid delivery conduit. The method also includes delivering fluid comprising at least one therapeutic agent under positive pressure through the conduit and into the portion of the ear.

The portion of the ear can include any one or more of an inner ear, a cochlea, an organ of Corti, and a basilar membrane. The therapeutic agent can include human atonal gene. In one embodiment, the method also includes delivering a cofactor to the portion of the ear to improve fluid delivery. The cofactor can include at least one of a corticosteroid impregnated in the scaffold, a corticosteroid coated onto the scaffold, and a propagation enhancing enzyme. In one embodiment, the method also includes allowing the scaffold to degrade within the portion of the ear and thereby release a corticosteroid impregnated in the scaffold.

In another aspect of at least one embodiment of the invention, a method of delivering a therapeutic agent during fetal surgery is provided that includes implanting a microfluidic convection-enhanced-delivery (CED) probe into a target region of a fetus or a patient in which the fetus is disposed, the probe comprising a degradable scaffold and a fluid delivery conduit. The method also includes delivering fluid comprising the therapeutic agent under positive pressure through the conduit and into the target region.

The target region can be or can include an umbilical cord, an umbilical artery, an umbilical vein, a placenta, and/or a uterine wall. In one embodiment, the therapeutic agent comprises stem cells.

In another aspect of at least one embodiment of the invention, a microfluidic convection-enhanced-delivery (CED) device is provided that includes an insertion support scaffold having a proximal end and a distal end, a shank coupled to the support scaffold, a first fluid delivery conduit extending longitudinally through the shank having an inlet port and at least one outlet port, and a second fluid delivery conduit extending longitudinally through the shank having an inlet port and at least one outlet port. The at least one outlet port of the second fluid delivery conduit is spaced longitudinally a distance apart from the at least one outlet port of the first fluid delivery conduit.

In some embodiments, the at least one outlet port of the second fluid delivery conduit is disposed closer to the distal end of the shank than the at least one outlet port of the first fluid delivery conduit. The scaffold can have a width in the range of about 0.02 µm to about 2000 µm and/or can be rigid, semi-rigid, and/or partially or fully degradable. The first and second fluid delivery conduits can each have a diameter in the range of about 0.02 µm to about 500 µm.

In some embodiments, the device can include an inflatable member coupled to the shank, an interior of the inflatable member being in fluid communication with the first fluid delivery conduit via the at least one outlet port of the first fluid delivery conduit. The inflatable member can be or can include a reinforced conformable balloon. The inflatable member can have at least a deflated configuration in which it occupies a first volume and an inflated configuration in which it occupies a second volume that is greater than the first volume.

The device can be MRI and stereotactic surgery compatible, can include at least one radiopaque marker, and/or can include a microsensor embedded in at least one of the first and second fluid delivery conduits.

In another aspect of at least one embodiment of the invention, a method of delivering a drug to a cavernous malformation within a patient is provided. The method includes implanting a microfluidic convection-enhanced-delivery (CED) probe into the cavernous malformation, the probe comprising an insertion scaffold and at least one fluid delivery conduit, and delivering fluid comprising the drug under positive pressure through the at least one fluid delivery conduit and into the cavernous malformation.

In some embodiments, the drug can include one or more antiangiogenesis compounds, such as celecoxib, bortezomib, interferon, and/or rapamycin. The drug can include nanoparticles encapsulated with therapeutic molecules or antiangiogenesis compounds.

In some embodiments, the at least one fluid delivery conduit comprises a first fluid delivery conduit having an outlet port formed therein and a second fluid delivery conduit having an outlet port formed therein. The probe can be implanted such that the outlet port of the first fluid delivery conduit is disposed at the surface of the cavernous malformation and the outlet port of the second fluid delivery conduit is disposed within the core of the cavernous malformation. The method can also include delivering the fluid under positive pressure to the surface of the cavernous malformation via the first fluid delivery conduit and to the core of the cavernous malformation via the second fluid delivery conduit.

The probe can be implanted such that the outlet port of the first fluid delivery conduit is disposed within the core of the cavernous malformation and the outlet port of the second fluid delivery conduit is disposed within the core of the cavernous malformation. The method can also include delivering the fluid under positive pressure to the core of the cavernous malformation via the second fluid delivery conduit and then inflating a balloon in fluid communication with the outlet port of the first fluid delivery conduit to apply pressure to the fluid and force it into the surrounding cavernous malformation.

In some embodiments, the drug can include a hydrogel or other substance having adhesive properties. The cavernous malformation can be formed in the central nervous system of the patient. The drug can be formulated to tamponade and/or completely coat the cavernous malformation. The probe can include a balloon at the distal end operable to compress the drug into the cavernous malformation. The method can include adjusting delivery of the fluid based on feedback from at least one microsensor embedded in the probe.

In another aspect of at least one embodiment of the invention, a method of delivering a therapeutic agent to a patient is provided. The method can include advancing a microfluidic convection-enhanced-delivery (CED) device into a target region of the patient, the CED device including an insertion support scaffold having a proximal end and a distal end, a shank coupled to the support scaffold, a first fluid delivery conduit extending longitudinally through the shank having an inlet port and at least one outlet port, and a second fluid delivery conduit extending longitudinally through the shank having an inlet port and at least one outlet port, the at least one outlet port of the second fluid delivery conduit being spaced longitudinally a distance apart from the at least one outlet port of the first fluid delivery conduit. The method can also include supplying a fluid comprising the therapeutic agent under positive pressure to at least one of the first and second fluid delivery conduits. The method can also include ejecting the fluid from at least one of the first and second fluid delivery conduits to deliver the fluid to the target region. The method can also include inflating an inflatable member in the target region to augment delivery of the therapeutic agent.

In some embodiments, the method can include allowing the scaffold to degrade and thereby release a corticosteroid impregnated in the scaffold. The method can be used to treat at least one condition selected from central-nervous-system (CNS) neoplasm, intractable epilepsy, Parkinson's disease, Huntington's disease, stroke, lysosomal storage disease, chronic brain injury, Alzheimer's disease, amyotrophic lateral sclerosis, balance disorders, hearing disorders, and cavernous malformations.

In another aspect of at least one embodiment of the invention, a method of fabricating a delivery device having at least one fluid channel is provided. The method can include depositing an oxide mask on a backside of a silicon wafer, patterning the oxide mask to define a perimeter of the delivery device, depositing a polyimide layer on a frontside of the silicon wafer, depositing sacrificial resist on the polyimide layer in a shape of the at least one fluid channel, depositing a parylene layer over the sacrificial resist and the polyimide layer, depositing an aluminum mask over the parylene layer, and removing the sacrificial resist using a solvent to form the at least one fluid channel between the polyimide layer and the parylene layer.

In some embodiments, the method can also include coupling a micro-capillary tube to the delivery device such that the micro-capillary tube is in fluid communication with the at least one fluid channel. The method can also include etching a trench into the backside of the silicon wafer according to the patterned oxide mask. The method can also include applying an oxide etch stop to the floor of the trench.

In another aspect of at least one embodiment of the invention, a method of fabricating a delivery device having at least one fluid channel is provided. The method can include etching a frontside of a silicon wafer to define a perimeter of the delivery device, applying a polyimide coat to the frontside of the silicon wafer and to a backside of the silicon wafer, applying sacrificial resist to the polyimide coat in a shape of the at least one fluid channel, applying a parylene layer over the sacrificial resist, depositing an aluminum mask over the parylene layer, and removing the sacrificial resist using a solvent to form the at least one fluid channel between the polyimide coat and the parylene layer.

In some embodiments, the method can also include coupling a micro-capillary tube to the delivery device such that the micro-capillary tube is in fluid communication with the at least one fluid channel.

In another aspect of at least one embodiment of the invention, a microfluidic convection-enhanced-delivery (CED) device is provided. The device can include a substrate that defines a body, an elongate distal tip, and first and second proximal legs. The device can also include a first fluid channel that extends along the first leg, along the body, and along the distal tip, and a second fluid channel that extends along the second leg, along the body, and along the distal tip. The device can also include a first micro-capillary tube coupled to the first leg portion and in fluid communication with the first fluid channel, and a second micro-capillary tube coupled to the second leg portion and in fluid communication with the second fluid channel. The device can also include a tubular sheath that encapsulates the first and second legs and at least a portion of the first and second micro-capillary tubes.

In some embodiments, the device can include a nose disposed at an interface between the distal tip and the body that encapsulates a distal portion of the body. The nose can be conical or hemispherical.

The present invention further provides devices, systems, and methods as claimed.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the methods, systems, and devices disclosed herein. One or more examples of these embodiments are illustrated in the accompanying drawings. Those skilled in the art will understand that the methods, systems, and devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The methods, systems, and devices disclosed herein generally involve convection-enhanced delivery of drugs to a target region within a patient. Microfluidic catheter devices are disclosed that are particularly suitable for targeted delivery of drugs via convection, including devices capable of multi-directional drug delivery and devices that control fluid pressure and velocity using the venturi effect. Methods of treating various diseases using such devices are also disclosed, including methods of treating cerebral and spinal cavernous malformations, cavernomas, and hemangiomas, methods of treating neurological diseases, methods of treatment using multiple microfluidic delivery devices, methods of treating hearing disorders, methods of spinal drug delivery using microfluidic devices, and methods of delivering stem cells and therapeutics during fetal surgery. Methods of manufacturing such devices are also disclosed.

The term "drug" as used herein refers to any functional agent that can be delivered to a human or animal patient, including hormones, stem cells, gene therapies, chemicals, compounds, small and large molecules, dyes, antibodies, viruses, therapeutic agents, etc. The terms "microfabricated CED device," "microfluidic delivery device," "CED device," "probe," "microprobe," "catheter," and "microcatheter" are generally used interchangeably herein.

Exemplary CED methods and devices are disclosed in U.S. Publication No. 2010/0098767, filed on Jul. 31, 2009, the entire contents of which are incorporated herein by reference.

Figure 1:
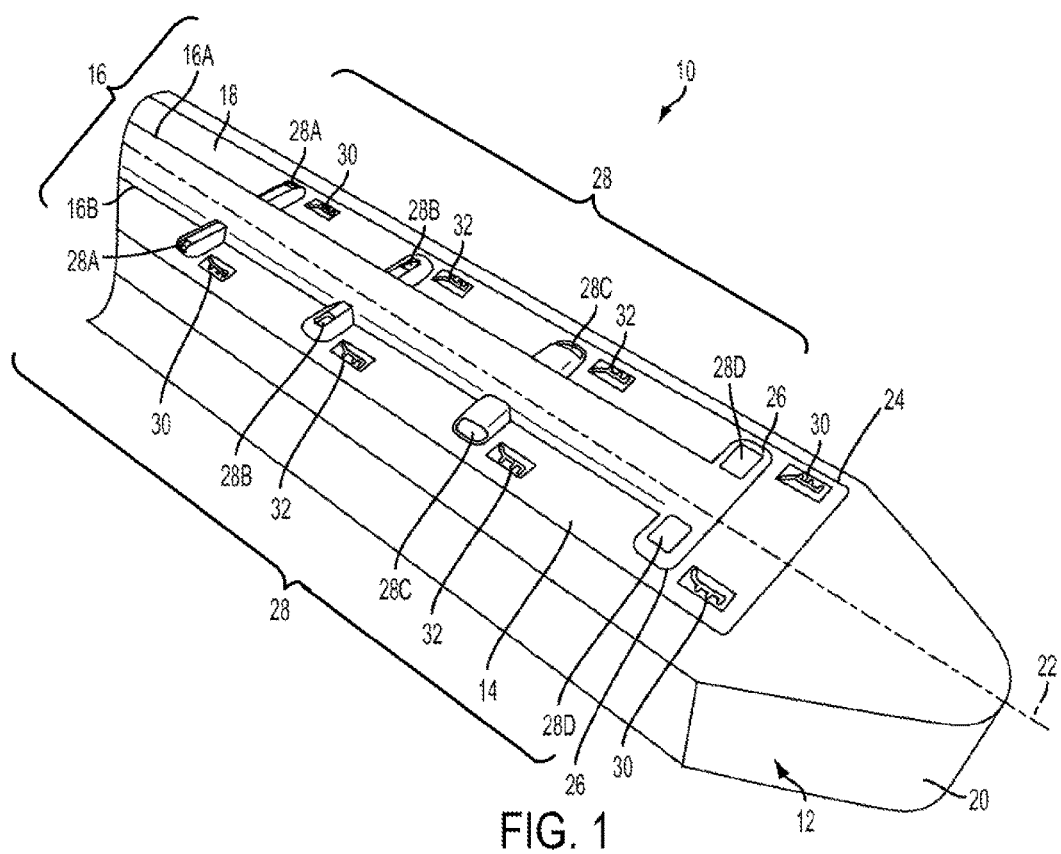
FIG. 1 is a perspective schematic view of one exemplary embodiment of a microfabricated CED device.

FIG. 1 illustrates one exemplary embodiment of a microfabricated CED device 10. The device 10 generally includes a support scaffold 12 to which one or more shank portions 14 are coupled. The shank portions 14 can include one of more fluid delivery conduits 16 formed thereon or therein.

The illustrated support scaffold 12 is generally formed by an elongate body having a proximal end 18, a distal end 20, and a longitudinal axis 22 extending therebetween. A cross-section of the illustrated scaffold 12 taken in a plane normal to the longitudinal axis 22 has a substantially rectangular shape, however any of a variety of cross-sectional shapes can be used, including circular, hexagonal, and elliptical. The scaffold 12 can provide structural rigidity to the device 10 to facilitate insertion into target tissue. To assist with tissue penetration and navigation, the distal end 20 of the support scaffold 12 can be tapered, pointed, and/or sharpened. In the illustrated embodiment, the scaffold 12 is provided with a rounded atraumatic tip so as to facilitate insertion through tissue without causing trauma to the tissue.

The support scaffold 12 can be rigid or semi-rigid and can be formed from a degradable thermoplastic polymer, for example, a degradable thermoplastic polyester or a degradable thermoplastic polycarbonate. In one embodiment, the support scaffold 12 is formed from poly(lactic-co-glycolic acid) (PLGA) and is configured to biodegrade within the target tissue. This can advantageously eliminate the need to remove the support scaffold 12 once the device 10 is positioned within target tissue, thereby avoiding the potential to disrupt the positioning of the fluid delivery conduits 16. Any of a variety of other materials can also be used to form the support scaffold 12, including silicon or various ceramics, metals, and plastics known in the art.

The support scaffold 12 can contain or can be impregnated with a quantity of a drug. Alternatively, or in addition, a surface of the support scaffold 12 can be coated with a drug. Exemplary drugs include anti-inflammatory components, drug permeability-increasing components, delayed-release coatings, and the like. In one embodiment, the scaffold 12 can be coated or impregnated with a corticosteroid such as dexamethasone which can prevent swelling around the injection site and disruptions to the fluid delivery pattern that can result from such swelling.

The scaffold 12 can have a width of approximately 100 μm to approximately 200 μm and can have a length that varies depending on the target tissue (e.g., depending on the depth at which the target tissue is situated). In one embodiment, the scaffold 12 is between 2 cm and 3 cm long.

The scaffold 12 can also include a recess or shelf portion 24 configured to retain or mate with the shank portion 14 of the device 10. In addition, as described further below, the scaffold 12 can include multiple recesses or shelf portions for coupling to a plurality of shank portions 14. In this case, the recesses or shelf portions can be formed on multiple different surfaces of the scaffold. A variety of techniques can be used to couple the shank portion 14 to the support scaffold 12, such as surface tension from a water drop, adhesives, and/or a biocompatible petroleum jelly.

The device 10 can also include one or more shank portions 14 that are matable to the support scaffold 12. The shank portion 14 can be a flexible substrate having one or more fluid delivery conduits 16 formed therein or thereon. The shank portion 14 can be formed from any of a variety of materials, such as silicon or Parylene.

One or more fluid delivery conduits 16 can be formed in or on the shank portion 14 of the device. The conduits 16 can extend along a surface of the shank portion 14 in a direction that is generally parallel to the longitudinal axis 22 of the scaffold 12, and can have one or more lateral portions 26 extending in a direction that forms a non-zero angle with the longitudinal axis 22.

Each conduit 16 can include a fluid inlet port (not shown in FIG. 1) and one or more fluid outlet ports 28. The fluid inlet port can be positioned at a proximal end of the device 10, and can allow the conduit 16 to be placed in fluid communication with a fluid reservoir, e.g., via one or more pumps, meters, valves, or other suitable control devices. Such control devices can be used to regulate the pressure at which fluid is supplied to the device 10, or the rate or volume of fluid that is supplied to the device 10.

Fluid supplied to the conduit 16 though the fluid inlet port is directed through an inner lumen of the conduit and released through the one or more fluid outlet ports 28. The fluid outlet ports 28 can be sized, shaped, and/or positioned to control various release parameters of the fluid. For example, the fluid outlet ports 28 can be configured to control the direction in which fluid is release from the device 10, the distribution of the fluid within the target tissue, and the velocity or pressure at which the fluid is released.

In the illustrated embodiment, the shank portion 14 includes first and second parylene conduits 16A, 16B extending therethrough. The conduits 16A, 16B include a longitudinal portion and a plurality of lateral extensions 26 in which fluid outlet ports 28 are formed. The size of the fluid outlet ports 28 progressively increases towards the distal end 20 of the device 10, which can advantageously compensate for pressure loss that occurs along the length of the device such that fluid is released from each of the plurality of fluid outlet ports 28 at substantially the same pressure. The illustrated fluid outlet ports 28 are also shaped to control the release direction of the fluid. The ports 28A and 28C open in a side or lateral direction, whereas the ports 28B and 28D open towards the top of the device 10.

The device can also include one or more sensors 30 mounted in or on the shank portion 14 or on the scaffold 12. The sensors 30 can include temperature sensors, pH sensors, pressure sensors, oxygen sensors, tension sensors, interrogatable sensors, glutamate sensors, ion concentration sensors, carbon dioxide sensors, lactate sensors, neurotransmitter sensors, or any of a variety of other sensor types, and can provide feedback to a control circuit which can in turn regulate the delivery of fluid through the device 10 based on one or more sensed parameters. One or more electrodes 32 can also be provided in or on the shank portion 14 or the support scaffold 12, which can be used to deliver electrical energy to target tissue, e.g., to stimulate the target tissue or to ablate the target tissue. In one embodiment, electrical energy is delivered through the electrodes 32 while a drug is simultaneously delivered through the fluid delivery conduits 16.

The device 10 can be used for CED of drugs to treat disorders of the brain, ears, other neural tissue, or other parts of a human or animal body. When used in the brain, the device 10 can circumvent the blood-brain barrier (BBB) by infusing drugs under positive pressure directly into tissue. The device 10 provides a number of advantages, such as 1) a smaller cross-sectional area compared with conventional needles used in CED; 2) less disturbance to tissue when inserted into the brain than conventional needles; 3) the elimination of backflow or reflux along the outside of the inserted part, which in turn, permits higher rates of drug delivery in the device 10 compared with conventional needles; 4) minimal or no occlusion of the fluid delivery conduits 16 during insertion into the brain; 5) multiple parylene conduits 16 can be fabricated into the silicon shank 14, each conducting a distinct fluid (drug), which allows simultaneous, sequential, or programmed delivery of multiple agents; 6) the device 10 has the potential to serve simultaneously as a drug delivery system and as a sensor-equipped probe to measure local tissue characteristics such as, but not limited to, pressure, pH, ion-specific concentrations, location, and other parameters; and 7) the device 10 allows for directional control of the drug release pattern.

The device 10 can be functionally attached to the distal end of a long, thin insertion vehicle such as a cannula or a needle in or on which a fluid attachment could be made to the fluid inlet ports of the device's fluid delivery conduits 16.

This can be especially advantageous in applications involving penetration of relatively thick tissue, e.g., insertion through a human skull.

In addition to delivering a drug-containing fluid, the device 10 can also be used to deliver enzymes or other materials to modify tissue permeability and improve drug distribution in the targeted tissue. For example, penetration of a drug-containing nanoparticles into brain tissue can be enhanced by enzymatic digestion of at least one brain extracellular matrix component and intracranial infusion of the nanoparticle into the brain tissue. In another embodiment, at least one enzyme can be immobilized to a surface of the nanoparticle during the step of enzymatic digestion. The device 10 can provide the ability to deliver enzymatic and/or other materials that can, e.g., modify the drug delivery site, and therapeutic materials, in virtually any order, sequencing, and/or timing without the need to use different delivery devices and the potential complications involved in doing so.

The device 10 can also be used to biopsy tissue, for example by passing a stylet or a grasping tool through one of the conduits 16 to a target site and then withdrawing the stylet or grasping tool from the target site with a biopsy specimen therein. In some embodiments, the shank portions 14 or the support scaffold 12 can have a larger-diameter lumen extending therethrough for biopsy purposes, with smaller fluid conduits 16 formed on the exterior thereof.

Figure 2A:
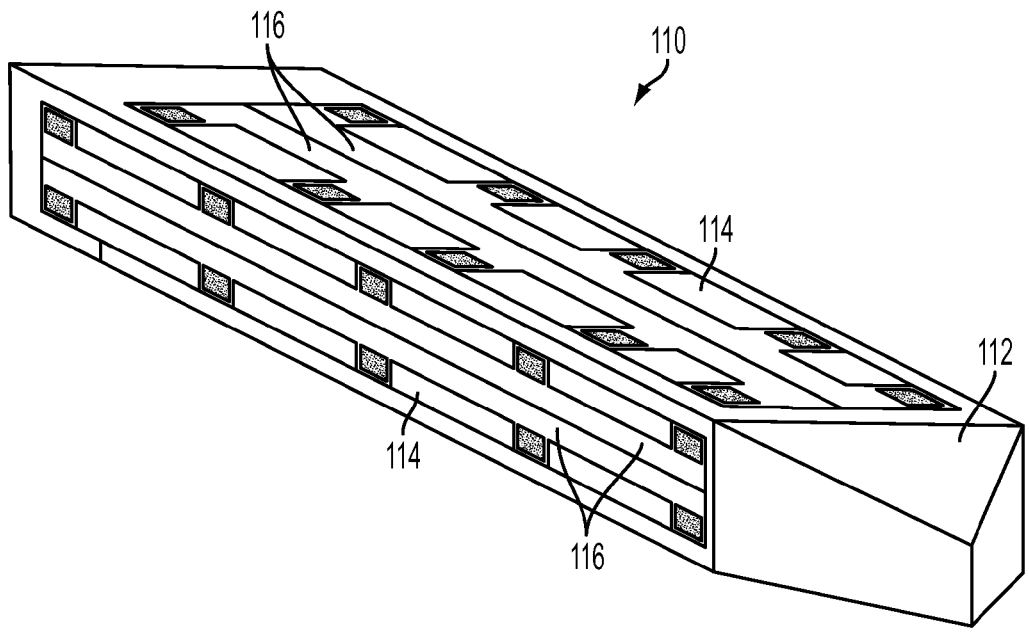
FIG. 2A is a perspective schematic view of another exemplary embodiment of a microfabricated CED device.
Figure 2B:
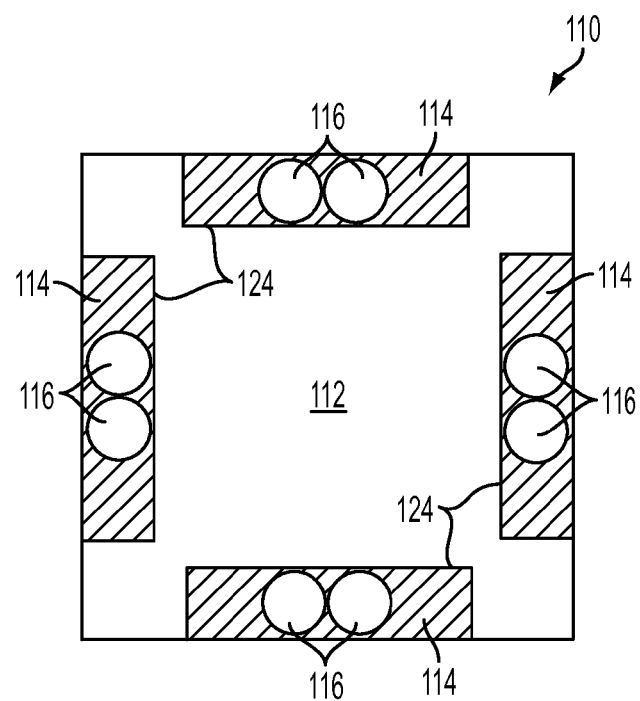
FIG. 2B is a cross-sectional view of the microfabricated CED device of FIG. 2A.

FIGS. 2A and 2B illustrate another exemplary embodiment of a microfabricated CED device 110. The device 110 includes a rectangular support scaffold 112 with shank portions 114 and accompanying fluid delivery conduits 116 coupled to each of the four side surfaces thereof. As shown in the cross-sectional view of FIG. 2B, the shank portions 114 are disposed within corresponding recesses 124 formed in the sidewalls of the support scaffold 112. In an alternative embodiment, the shank portions 114 can be surface mounted on the scaffold 112. Positioning of shank portions 114 and fluid delivery conduits 116 on each of the four side surfaces of the scaffold 112 can further facilitate 360 degree convective flow of drug-containing fluid from the device 110.

The structure and function of the device 110 is otherwise substantially the same as that of the device 10 described above, and therefore a further description thereof is omitted here for the sake of brevity.

Figure 3A:
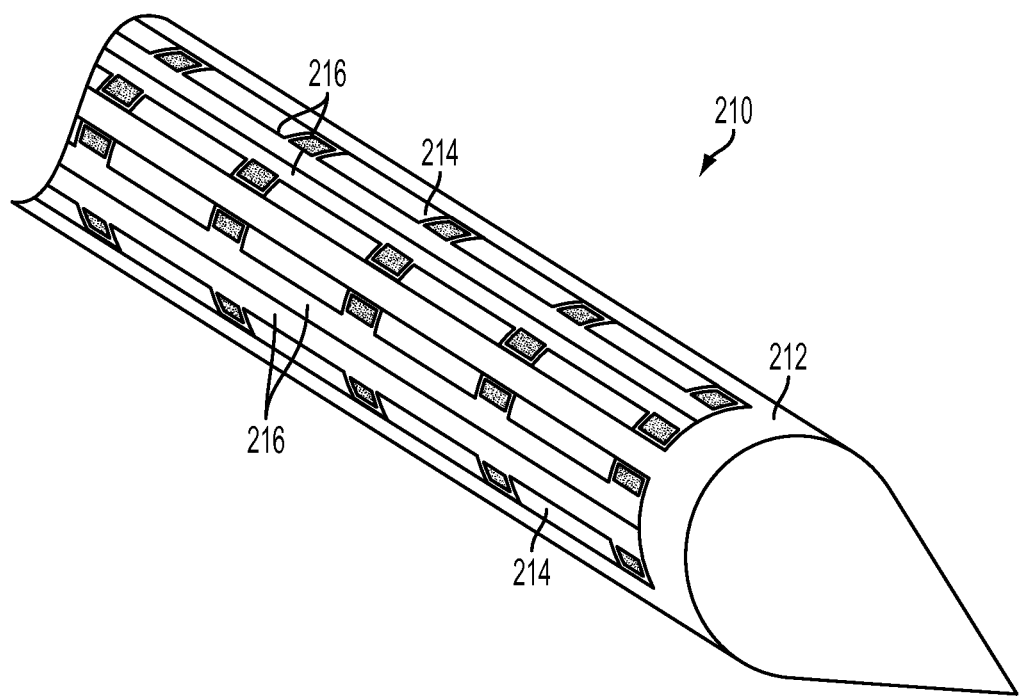
FIG. 3A is a perspective schematic view of another exemplary embodiment of a microfabricated CED device.
Figure 3B:
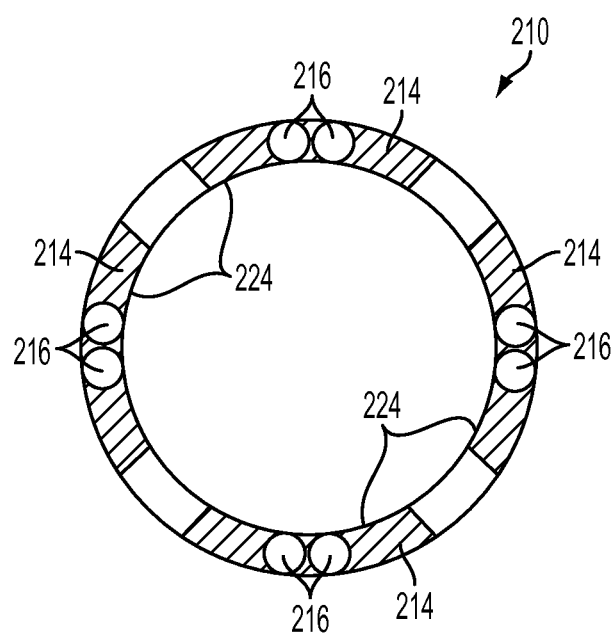
FIG. 3B is a cross-sectional view of the microfabricated CED device of FIG. 3A.

FIGS. 3A and 3B illustrate another exemplary embodiment of a microfabricated CED device 210. The device 210 includes a cylindrical support scaffold 212 with shank portions 214 and accompanying fluid delivery conduits 216 coupled in a spaced relationship about the outer surface of the scaffold 212. As shown in the cross-sectional view of FIG. 3B, the shank portions 214 are disposed within corresponding recesses 224 formed in the sidewalls of the support scaffold 212. In an alternative embodiment, the shank portions 214 can be surface mounted on the scaffold 212. It will be appreciated that the flexible nature of the shank portions 214 and the fluid delivery conduits 216 permits them to be curved or otherwise contoured to match the surface profile of the scaffold 212. Positioning of shank portions 214 and fluid delivery conduits 216 about the outer surface of the scaffold 212 as shown can further facilitate 360 degree convective flow of drug-containing fluid from the device.

The structure and function of the device 210 is otherwise substantially the same as that of the device 10 described above, and therefore a further description thereof is omitted here for the sake of brevity.

Figure 4:
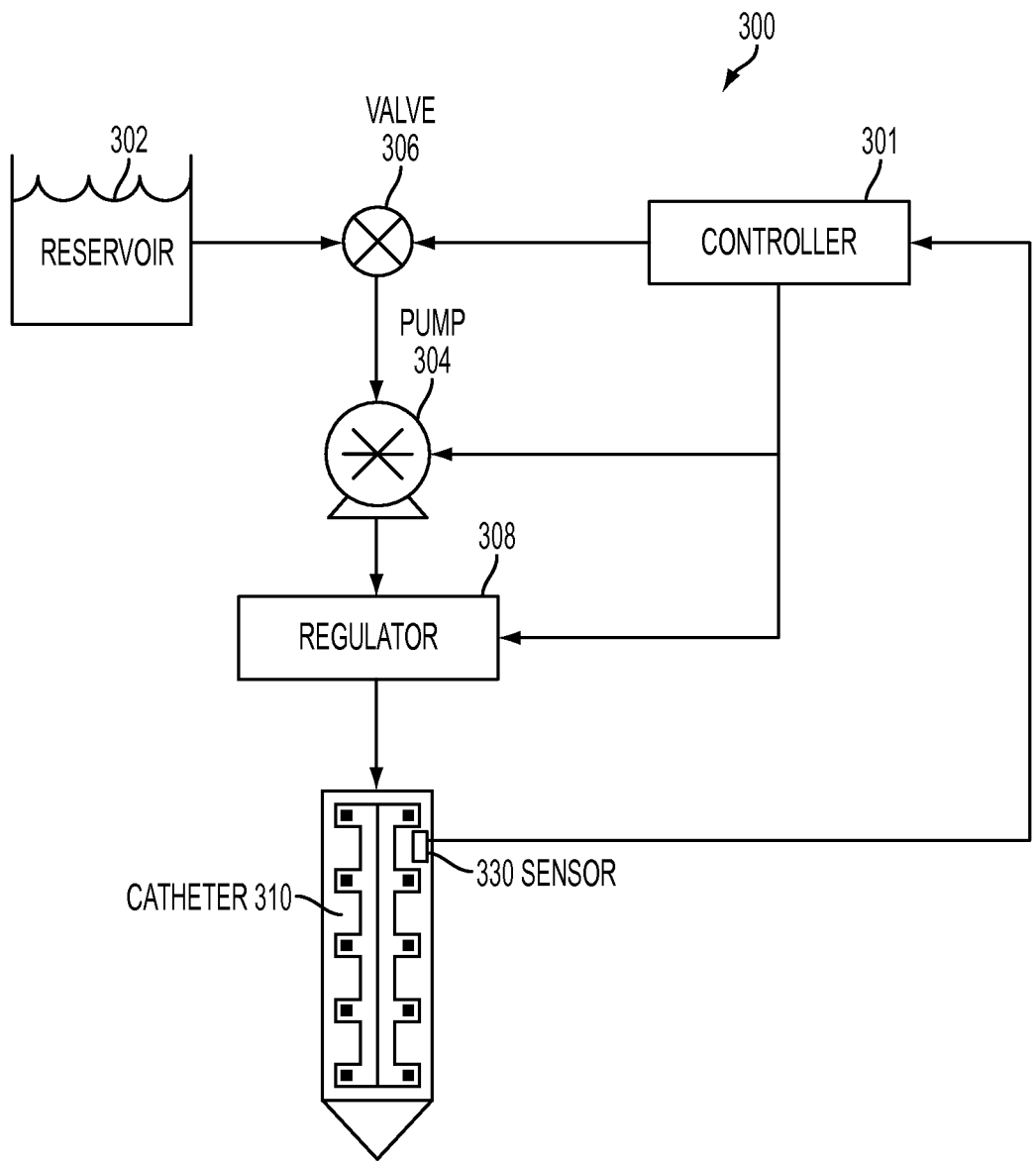
FIG. 4 is a schematic diagram of a fluid delivery system operatively coupled to a microfabricated CED device.

FIG. 4 is a schematic illustration of a drug delivery system 300 that includes a microcatheter CED device 310 which can be any of the devices 10, 110, 210 described above. The system 300 includes a reservoir 302 of a drug-containing fluid that is coupled to a pump 304 via a control valve 306. When the control valve is opened, fluid in the reservoir 302 is supplied under pressure by the pump 304 to a pressure regulator 308, which can adjust a pressure at which the fluid is supplied to the catheter 310. The control valve 306, pump 304, and regulator 308 can be operatively coupled to a controller 301 which can include a microprocessor and a memory and can be configured to execute a drug-delivery control program stored in a non-transitory computer-readable storage medium. The controller 301 can be configured to open or close the valve 306, to turn the pump 304 on or off, to change an output pressure of the pump 304, and/or to adjust a pressure set point of the regulator 308. The controller 301 can also receive information indicative of a sensed parameter via a feedback loop that includes one or more sensors 330 mounted in or on the catheter 310. Thus, in response to feedback from one or more sensors 330 implanted with the catheter 310, the controller 301 can start or stop the flow of fluid to the catheter 310, increase or decrease the pressure at which fluid is supplied to the catheter 310, etc. In one embodiment, the catheter 310 includes a pressure sensor 330 that measures a fluid pressure in the vicinity of the catheter 310 and the controller 301 is configured to maintain the fluid supply pressure at a substantially constant level based on feedback from the pressure sensor 330.

Figure 5A:
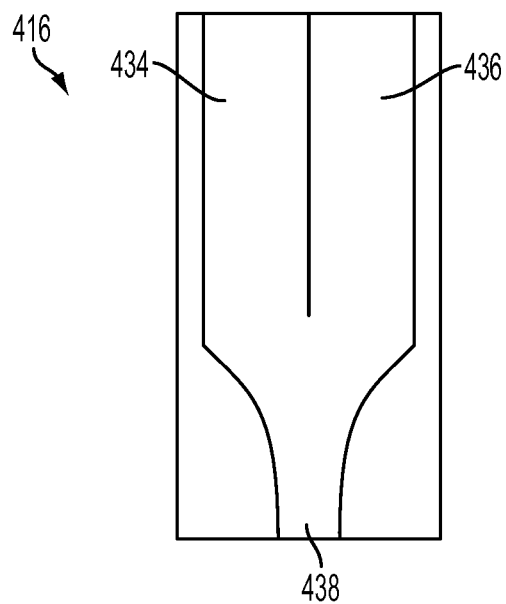
FIG. 5A is a schematic top view of one exemplary embodiment of a fluid delivery conduit of a microfabricated CED device.
Figure 5B:
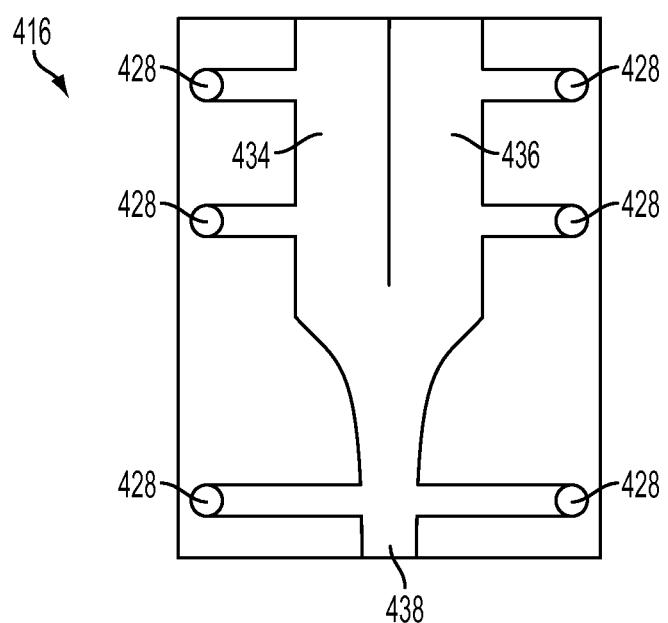
FIG. 5B is a schematic top view of another exemplary embodiment of a fluid delivery conduit of a microfabricated CED device.

FIGS. 5A and 5B illustrate an alternative embodiment of a fluid delivery conduit that can be used with the devices described herein. In FIG. 5A, the fluid delivery conduit 416 includes first and second upstream lumens 434, 436 which merge into a single downstream lumen 438. The inside dimension of the combined lumens 434, 436 decreases gradually at the merge, which can advantageously increase the velocity of fluid flowing through the downstream lumen 438. In the illustrated embodiment, the cross-sectional area of the downstream lumen 438 is less than the cross-sectional area of the first upstream lumen 434 and less than the cross-sectional area of the second upstream lumen 436, such that a flow restriction is formed in the delivery conduit 416.

Preferably, the constricted region formed by the downstream lumen 438 has a cross-sectional area that is approximately 20% less than the cross-sectional area of a proximally-adjacent portion of the delivery conduit 416. More preferably, the constricted region has a cross-sectional area that is approximately 30% less than the cross-sectional area of the proximally-adjacent portion of the delivery conduit. Even more preferably, the constricted region has a cross-sectional area that is approximately 40% less than the cross-sectional area of the proximally-adjacent portion of the delivery conduit.

In one embodiment, the proximally-adjacent portion has a height between about 1 micron and about 50 microns and the constricted region has a height between about 1 micron and about 25 microns. In another embodiment, the proximally-adjacent portion has a width between about 10 microns and about 100 microns and the constricted region has a width between about 5 microns and about 50 microns.

This "step-down advantage" described above provides additional pressure and velocity control for tailoring the delivery profile of the device. As shown in FIG. 5B, a plurality of outlet ports 428 can be disposed in fluid communication with the first and second upstream lumens 434, 436, and/or in fluid communication with the downstream lumen 438.

Figure 6:
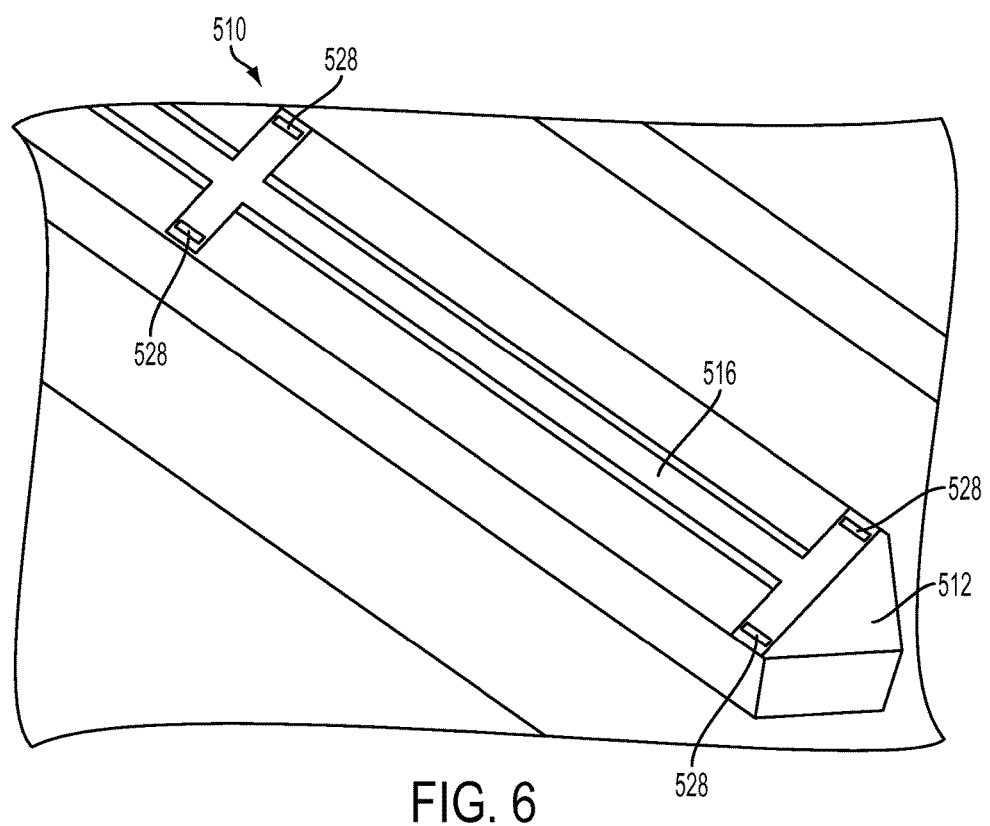
FIG. 6 is a electron micrograph of another exemplary embodiment of a microfabricated CED device.

FIG. 6 is a an electron micrograph of one exemplary embodiment of a microfabricated CED device 510 having a single fluid delivery conduit 516 mounted on a single surface of a degradable scaffold 512. As shown, the fluid delivery conduit 516 is approximately 25 μm wide and the fluid outlet ports 528 are spaced approximately 500 μm apart in the lengthwise direction.

Figure 7:
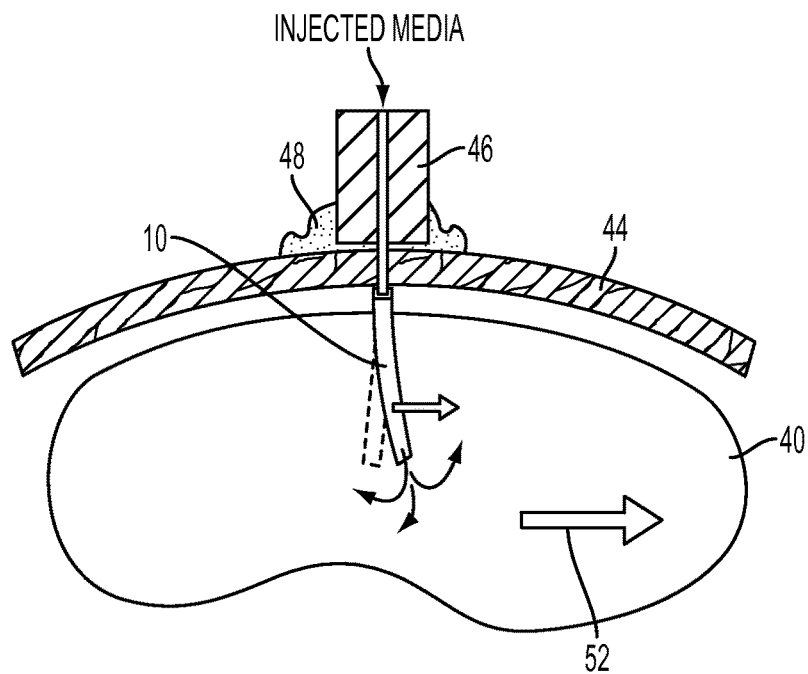
FIG. 7 is a schematic diagram of a microfabricated CED device implanted into a brain of a patient.

The devices disclosed herein can be used to deliver a drug-containing fluid under positive pressure to a target tissue region. FIG. 7 illustrates one exemplary method for convection-enhanced delivery of a drug to target tissue in a patient's brain 40. After appropriate site preparation and cleaning, a tissue opening can formed through the patient's scalp and skull 44 to expose the brain 40. Before or after forming the tissue opening, a pedestal 46 can optionally be mounted to the patient as shown using an epoxy or other adhesive 48. The pedestal 46 can support a CED device 10 while it is inserted, and can be particularly useful in long-term implantations.

Figure 8:
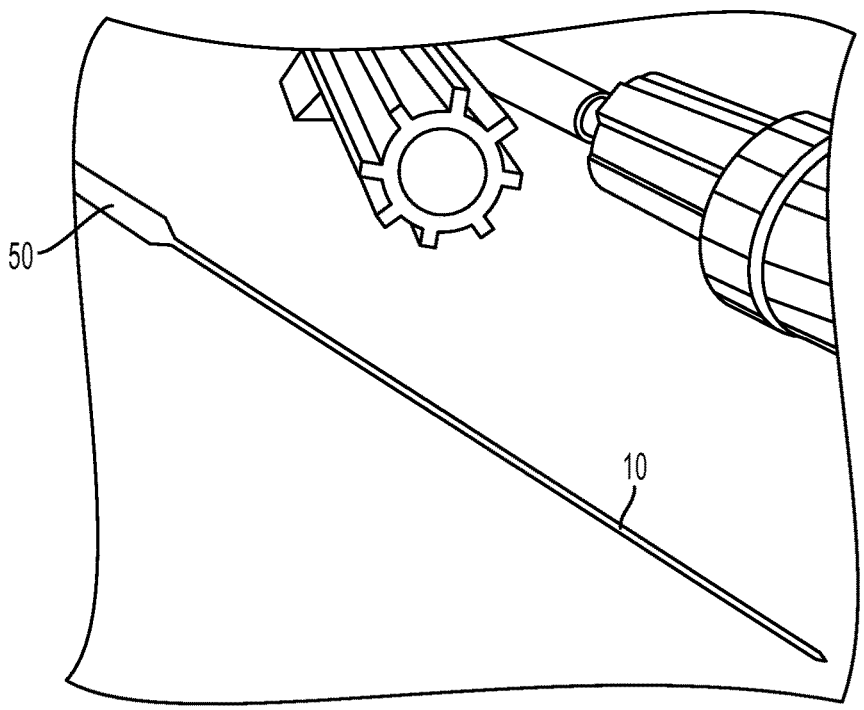
FIG. 8 is a perspective view of a microfabricated CED device coupled to a standard cannula.

The CED device 10 can optionally be coupled to a cannula 50 with a microfabricated interface for mating with the CED device 10, as shown in FIG. 8. Any of a variety of cannulas can be used, including standard cannulas configured to mate to a stereotactic frame in guided surgery. In some embodiments, the cannula can include a flexible catheter suitable for extended (e.g., 30 day) implantation. The catheter can be about 15 cm long and about 2 cm in diameter. The cannula can include a tubing portion that is approximately 6 feet in length with connectors for fluid and biosensor interface at the proximal end.

Referring again to FIG. 7, the CED device 10 can be advanced through the tissue opening and into the brain 40. As explained above, the scaffold 12 of the CED device 10 can be rigid and can include a pointed or sharpened tip 20 to facilitate penetration through the brain tissue towards the target region. One or more radiopaque markers can be included in the CED device 10 to permit radiographic imaging (e.g., to confirm proper placement of the CED device 10 within or in proximity to the target tissue). In embodiments in which a degradable scaffold 12 is used, the scaffold 12 can degrade shortly after insertion to leave behind only the flexible shank portion 14 and the fluid delivery conduits 16 mounted thereon. The flexible nature of the shank 14 permits the CED device 10 to move with the brain 40 if the brain 40 shifts within the skull 44 (e.g., in the direction of arrow 52), which prevents localized deformation of brain tissue adjacent to the CED device 10 that might otherwise occur with a rigid device. Such deformation can lead to backflow of the pressurized fluid along the surface of the device, undesirably preventing the fluid from reaching the target tissue.

Figure 9:
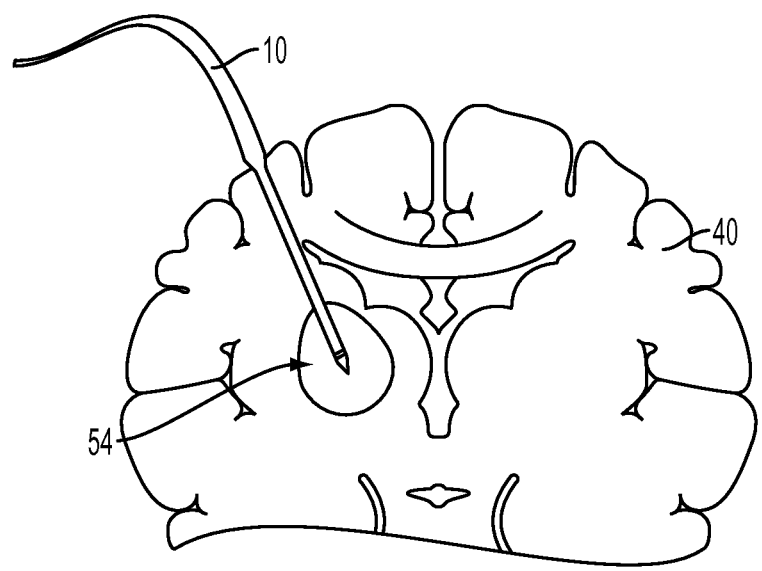
FIG. 9 is a schematic diagram of a microfabricated CED device implanted into a brain of a patient and an associated fluid release spatial distribution pattern.

Once the CED device 10 is positioned within or adjacent to the target tissue, injected media (e.g., a drug-containing fluid) can be supplied under positive pressure to the CED device 10 through one or more fluid inlet ports of one or more fluid delivery conduits 16 of the device 10. As shown in FIG. 9, the injected media is expelled under pressure from the fluid outlet ports of the fluid delivery conduits of the device 10 in the target region of tissue. The delivery profile 54 can be adjusted by varying parameters such as outlet port size, outlet port shape, delivery conduit size, delivery conduit shape, fluid supply pressure, fluid velocity, etc.

Figure 10:
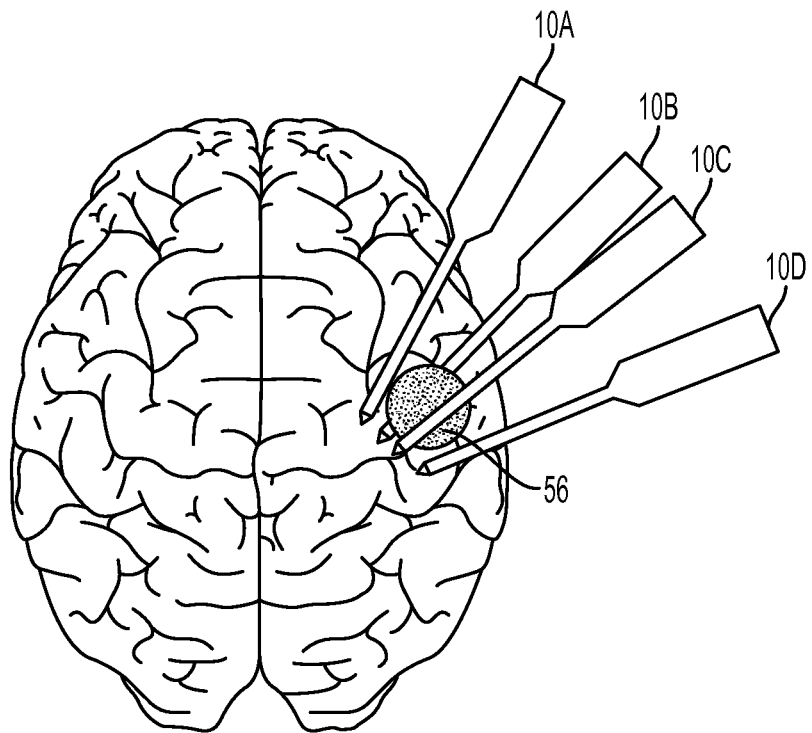
FIG. 10 is a schematic diagram of a plurality of microfabricated CED devices positioned to surround a target site within a brain of a patient.

Drug delivery can be further enhanced by strategic positioning of the CED device, and/or by using a plurality of CED devices. For example, as shown in FIG. 10, a plurality of CED probes 10A, 10B, 10C, and 10D can be positioned in a spaced relationship around a target site 56 (e.g., a tumor) such that one or more fluid outlet ports formed in each of the plurality of CED devices are aligned with the target site. In this example, CED devices having fluid outlet ports that are sized and positioned for directional fluid release can be oriented (e.g., with radiographic assistance) such that the direction of release is aimed towards the target tissue. One or more drug-containing fluids can then be delivered under positive pressure from the plurality of CED devices to the target site such that the drug substantially surrounds and saturates the target site or is delivered on several sides of the target site. The pressure at which fluid is supplied, or any of a variety of other delivery parameters, can be independently controlled for each of the plurality of CED devices, e.g., based on feedback from one or more microsensors disposed on the CED devices. For example, in the illustrated embodiment in which four CED devices are implanted to surround a target site, a controller can be configured to increase or decrease the fluid pressure for each of the four CED devices based on feedback from pressure sensors affixed thereto, such that the release pressure of each of the four CED devices is maintained at substantially the same level.

The plurality of CED devices can be inserted through a single tissue opening, or a plurality of separate tissue openings can be formed to facilitate insertion of the plurality of CED devices.

Figure 11:
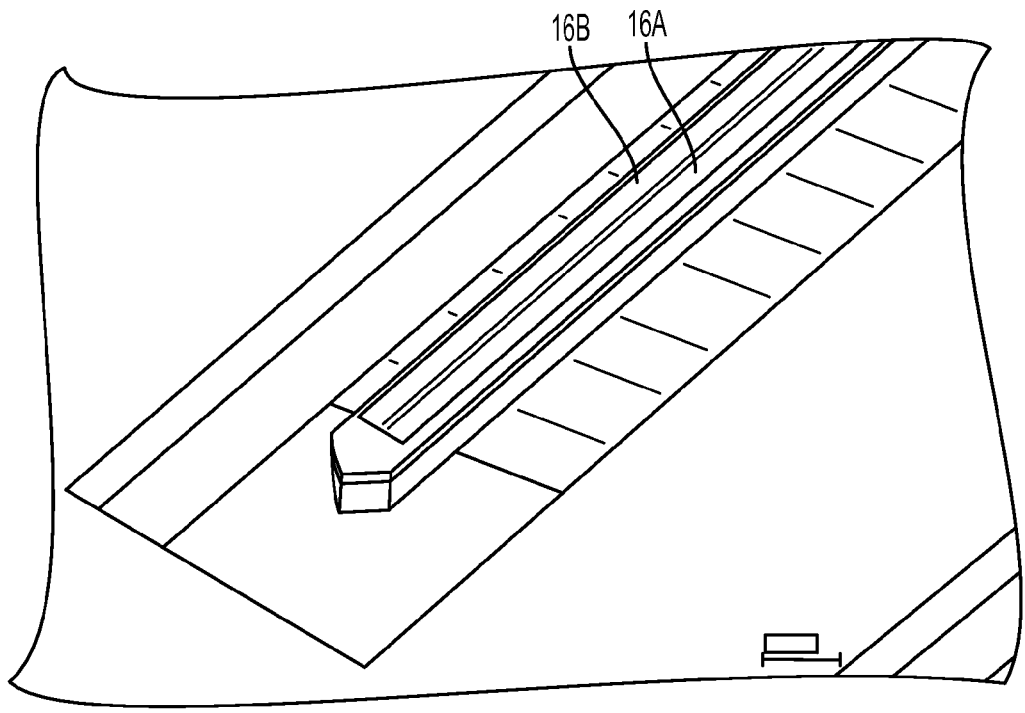
FIG. 11 is an electron micrograph of another exemplary embodiment of a microfabricated CED device.

As shown in FIG. 11, CED devices having a plurality of fluid delivery conduits can advantageously be used to deliver one or more cofactors along with the drug-containing fluid. For example, anti-inflammatory agents, enzymes, and various other functional agents can be delivered though a secondary conduit 16B before, during, or after delivery of the drug-containing fluid through a primary conduit 16A. Additional fluid delivery conduits can also be used for sensing or monitoring.

It will be appreciated from the foregoing that the methods and devices disclosed herein can provide convection-enhanced delivery of functional agents directly to target tissue within a patient. This convection-enhanced delivery can be used to treat a broad spectrum of diseases, conditions, traumas, ailments, etc.

Central-nervous-system (CNS) neoplasm, for example, can be treated by delivering an antibody (e.g., an anti-epidermal growth factor (EGF) receptor monoclonal antibody) or a nucleic acid construct (e.g., ribonucleic acid interference (RNAi) agents, antisense oligonucleotide, or an adenovirus, adeno-associated viral vector, or other viral vectors) to affected tissue.

In another exemplary embodiment, epilepsy can be treated by delivering an anti-convulsive agent to a target region within the brain. In another embodiment, Parkinson's disease can be treated by delivering a protein such as glial cell-derived neurotrophic factor (GDNF). In a further embodiment, Huntington's disease can be treated by delivering a nucleic acid construct such as a ribonucleic acid interference (RNAi) agent or an antisense oligonucleotide.

The methods and devices disclosed herein can also be used to deliver a neurotrophin under positive pressure to treat stroke, and/or to deliver a protein such as a lysosomal enzyme to treat lysosomal storage disease.

In another embodiment, the disclosed methods and devices can be used to treat Alzheimer's disease by delivering anti-amyloids and/or nerve growth factor (NGF) under positive pressure. In a further embodiment, amyotrophic lateral sclerosis can be treated by delivering a protein such as brain-derived neurotrophic factor (BDNF) or ciliary neurotrophic factor (CNTF) under positive pressure to the brain, spinal canal, or elsewhere in the central nervous system.

Chronic brain injury can be treated by delivering a protein such as brain-derived neurotrophic factor (BDNF) and/or fibroblast growth factor (FGF) under positive pressure in accordance with the methods and devices disclosed herein.

It will be appreciated that use of the devices disclosed herein and the various associated treatment methods is not limited to the brain of a patient. Rather, these methods and devices can be used to deliver a drug to any portion of a patient's body, including the spine.

Figure 12:
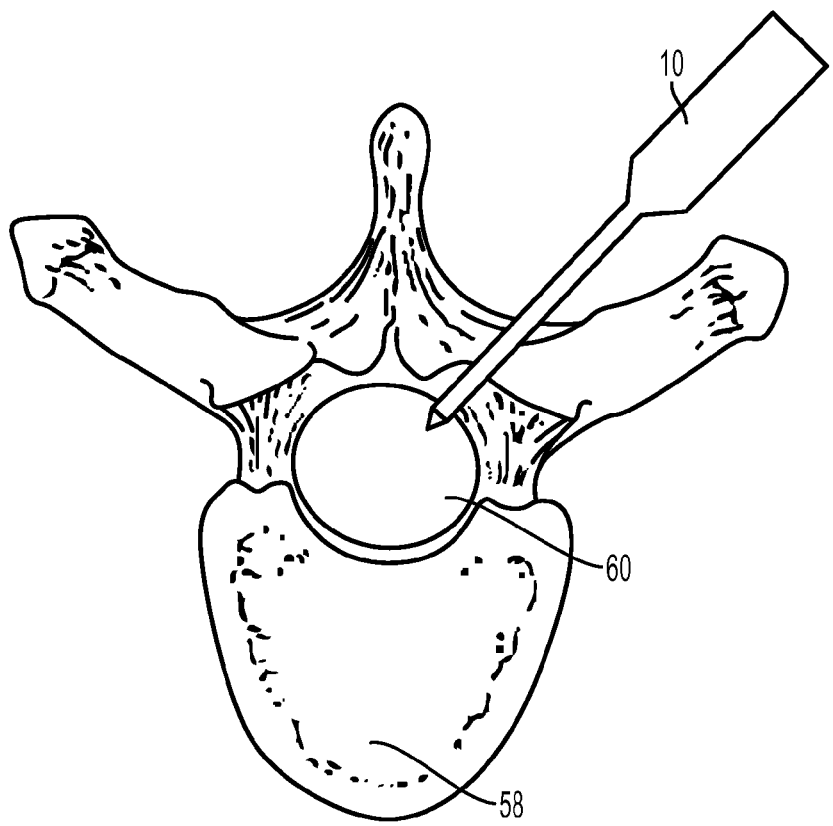
FIG. 12 is a schematic diagram of a microfabricated CED device implanted into a spinal canal of a patient.

As shown in FIG. 12, a CED device 10 can be inserted through a tissue opening formed adjacent to a vertebra 58 of a patient so as to facilitate delivery of a therapeutic agent to a target region within a spinal canal 60 of the patient. Traditional methods of delivering drug-containing fluid to the spinal canal result in the fluid mixing with the cerebrospinal fluid (CSF) of the patient, which carries the drug away from the target tissue and can lead to complications when the drug acts in non-target areas of the patient. The minimal size of the CED devices disclosed herein, coupled with the high flow rate of drug-containing fluid, on the other hand, allows for extremely precise targeting of the drug delivery, such that delivery into the cerebrospinal fluid (CSF) of the patient can be avoided, while still allowing delivery into specific target regions of the spinal canal. In one embodiment, stem cells can be delivered into the spinal canal or elsewhere in the central nervous system, for example to treat ALS.

Figure 13:
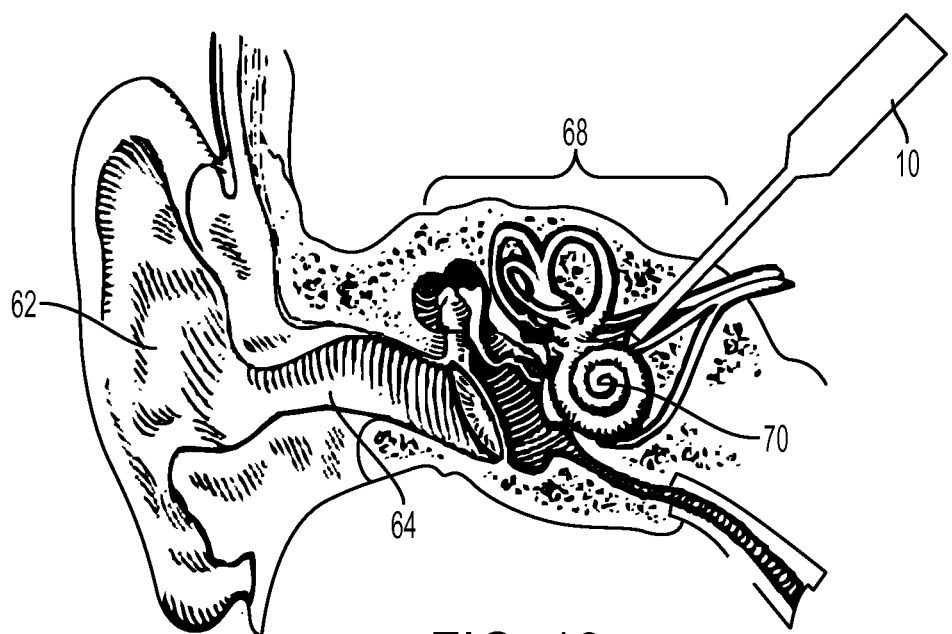
FIG. 13 is a schematic cross-sectional view of a microfabricated CED device implanted into an inner ear of a patient.
Figure 14:
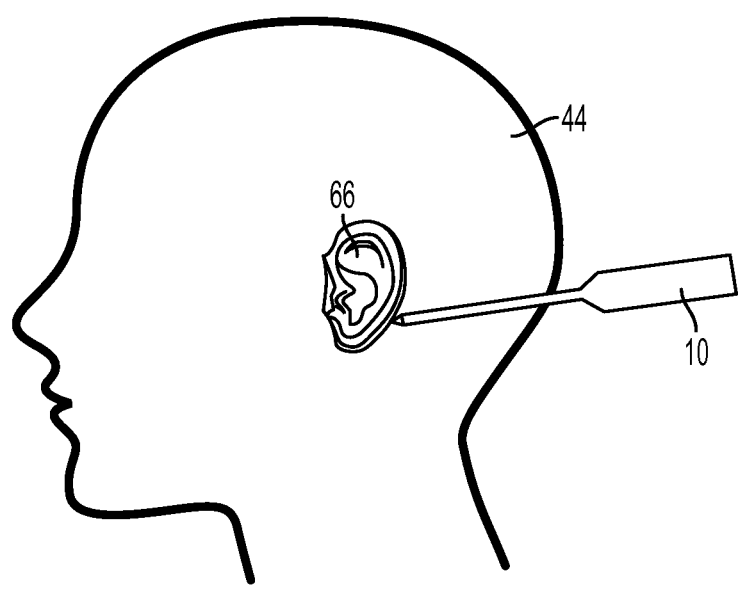
FIG. 14 is a schematic side view of a microfabricated CED device implanted into an inner ear of a patient.

The methods and devices disclosed herein can also be used to treat balance or hearing disorders by injecting a drug-containing fluid directly into a portion of a patient's ear. Existing techniques for delivering a drug to the inner ear require entry through the outer ear 62 and the ear canal 64, which can cause damage to the delicate structures of the ear. In the present embodiment, as shown in FIGS. 13-14, a tissue opening can instead be formed in the skull 44 behind a patient's ear 66 to allow insertion of a CED device 10. The device 10 can be inserted through the tissue opening and into the target portion of the patient's ear (e.g., inner ear 68, cochlea 70, organ of Corti, and/or basilar membrane). A drug-containing fluid can then be delivered through the device 10 under positive pressure to the target ear portion. Any of a variety of drugs can be used to treat the ear, including human atonal gene.

Figure 15:
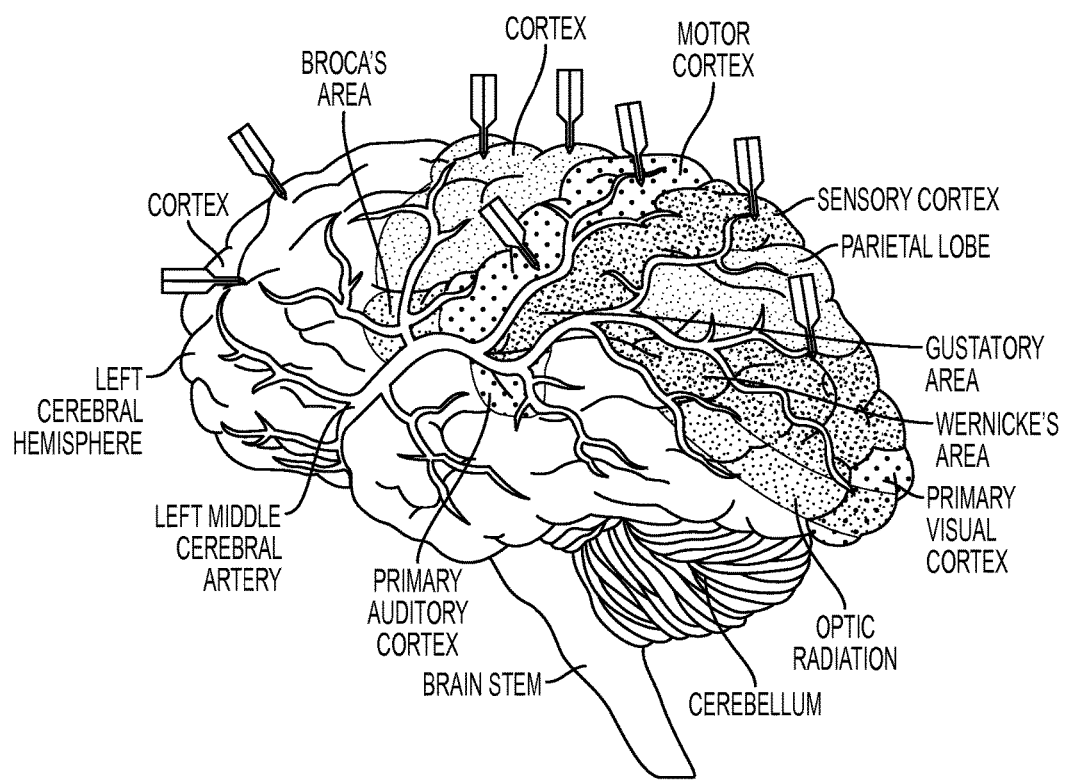
FIG. 15 is a schematic view of microfabricated CED devices implanted into various regions of a brain.

As shown in FIG. 15, the methods and devices disclosed herein can be used to treat Alzheimer's Disease or other neurological conditions by delivering a drug-containing fluid to the cerebral cortex. The drug-containing fluid can be delivered to any of a variety of regions of the brain, either individually or together and either simultaneously or sequentially. These regions can include the auditory cortex, the inferotemporal cortex, the prefrontal cortex, the premotor cortex, the primary motor cortex, the supplementary motor cortex, the somatosensory cortex, the parietal cortex, the visual cortex, the gustatory cortex, etc.

Figure 16:
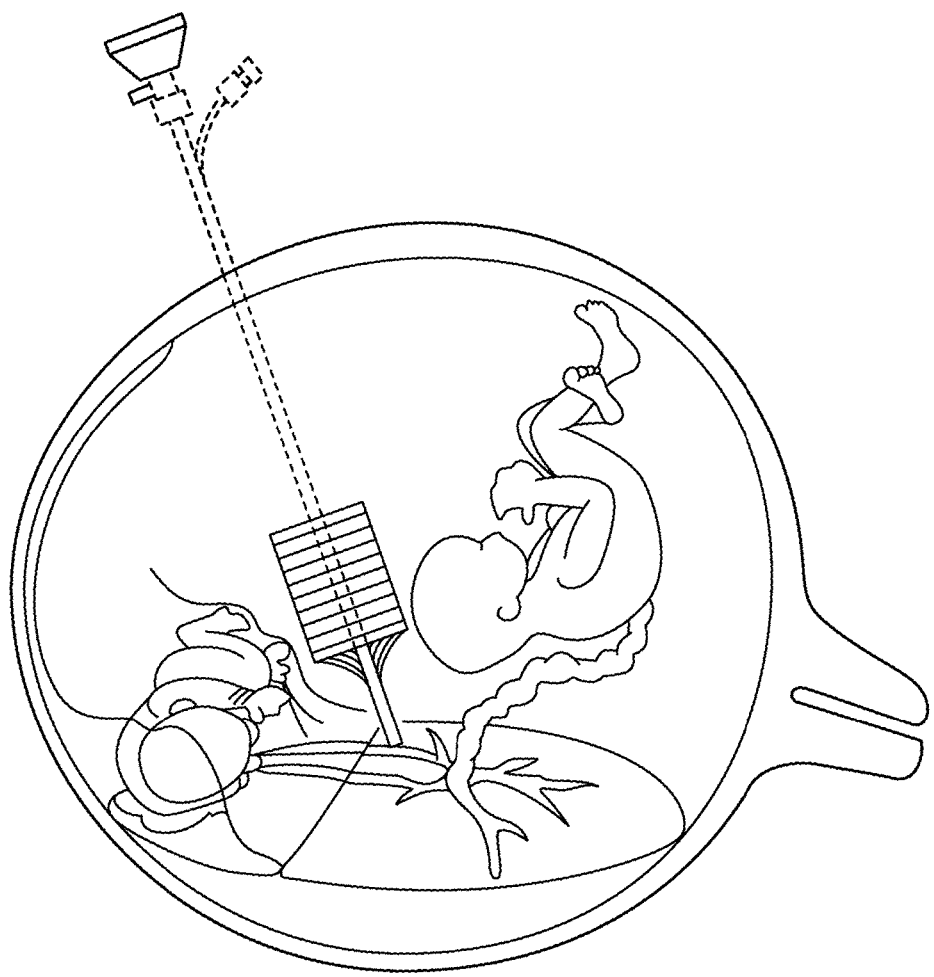
FIG. 16 is a schematic view of a microfabricated CED device implanted into a target region during fetal surgery.

As shown in FIG. 16, the methods and devices disclosed herein can also be used to deliver therapeutics (such as stem cells) to a fetus or to a patient in which the fetus is disposed. This can be particularly advantageous in delivering therapeutics during fetal surgery. As shown, a micro-fluidic CED device can be used to deliver a drug-containing fluid to an umbilical cord, an umbilical artery, an umbilical vein, a placenta, and/or a uterine wall.

Figure 17A:
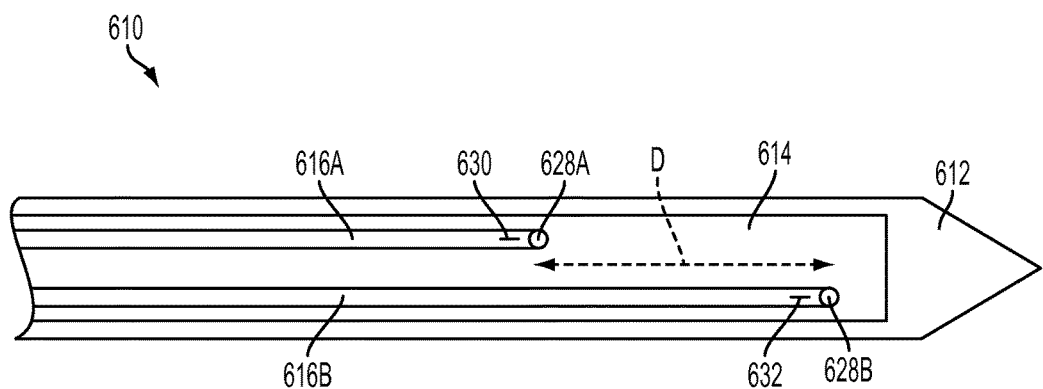
FIG. 17A is a schematic view of a microfabricated CED device having fluid delivery conduits with longitudinally staggered outlet ports.

FIG. 17A illustrates another exemplary embodiment of a microfluidic CED device 610 that includes a support scaffold 612, at least one shank 614, and at least first and second fluid delivery conduits 616A, 616B. The fluid delivery conduits 616A, 616B have differing lengths, such that the outlet ports 628A, 628B of the fluid delivery conduits are staggered longitudinally along the shank 614. In other words, the first and second fluid delivery conduits 616A, 616B terminate at a distance D apart from one another such that the outlet ports 628A, 628B thereof are staggered in the longitudinal direction. In an exemplary embodiment, the distance D is between about 0.02 μm and about 100 mm, and preferably between about 0.1 μm and about 10 mm. The device 610 can also include one or more sensors 630 and/or electrodes 632, as described above. The structure and function of the device 610 is otherwise substantially the same as that of the device 10 described above, and therefore a further description thereof is omitted here for the sake of brevity.

In use, the device 610 can be inserted into a target region (e.g., a cavernous malformation with a patient's central nervous system) such that the outlet port 628B of the second fluid delivery conduit 616B is disposed within a central portion of the target region (e.g., the core of the cavernous malformation) and such that the outlet port 628A of the first fluid delivery conduit 616A is disposed within a peripheral portion of the target region (e.g., the exterior surface of the cavernous malformation). Accordingly, the target region can be treated both from the inside-out and from the outside-in. In the case of a cavernous malformation, the device 610 can allow a drug to be delivered into the core of the cavernous malformation as well as to the surface of the cavernous malformation where the vascular-type cells are proliferating.

Figure 17B:
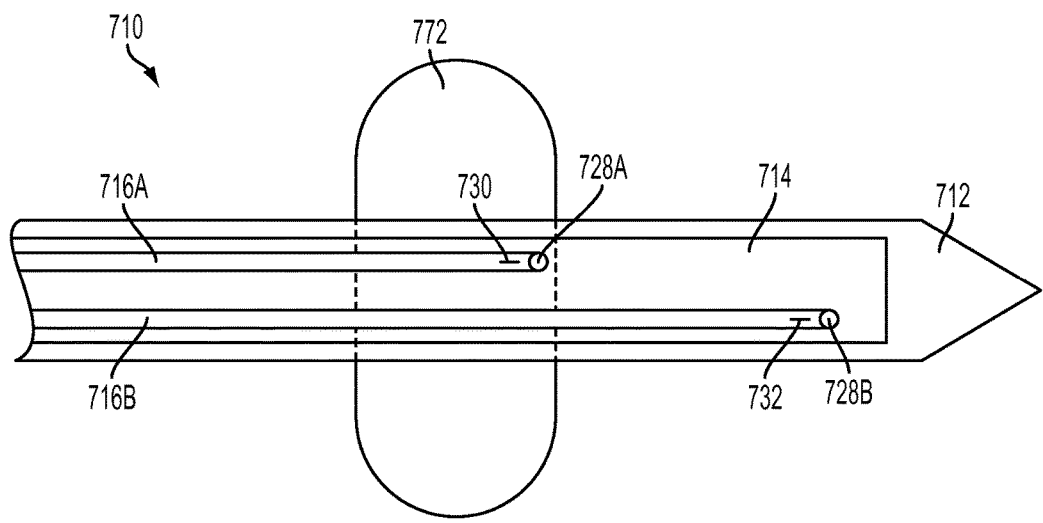
FIG. 17B is a schematic view of a microfabricated CED device having longitudinally staggered outlet ports and an inflatable member.

FIG. 17B illustrates another exemplary embodiment of a microfluidic CED device 710. The device 710 is substantially identical to the device 610 of FIG. 17A, except that an inflatable member 772 (e.g., a reinforced and/or conformable balloon) is included in the device 710. The inflatable member 772 can be in fluid communication with the first fluid delivery conduit 716A, such that fluid can be supplied through the first fluid delivery conduit 716A to inflate the inflatable member 772 and increase the volume of the inflatable member 772 or increase the pressure within the inflatable member 772. Similarly, fluid can be withdrawn from the inflatable member 772 via the first fluid delivery conduit 716A to reduce the volume of the inflatable member 772 or reduce the pressure therein. The inflatable member 772 can be coupled to an exterior of the device 710 (e.g., such that it substantially surrounds a portion of the device 710), or can be configured to deploy from within a recess formed in the device 710. The structure and function of the device 710 is otherwise substantially the same as that of the device 10 described above, and therefore a further description thereof is omitted here for the sake of brevity.

Figure 18A:
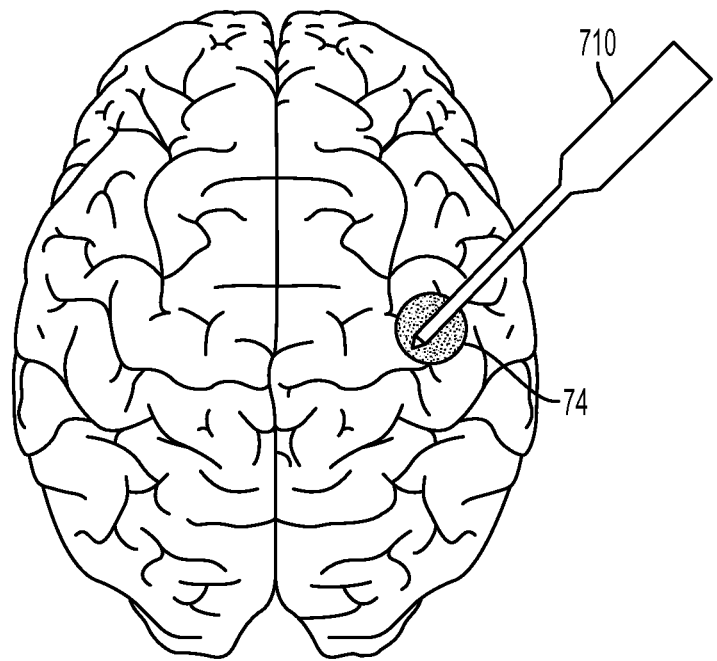
FIG. 18A is a schematic view of the device of FIG. 17B inserted into a cavernous malformation.
Figure 18B:
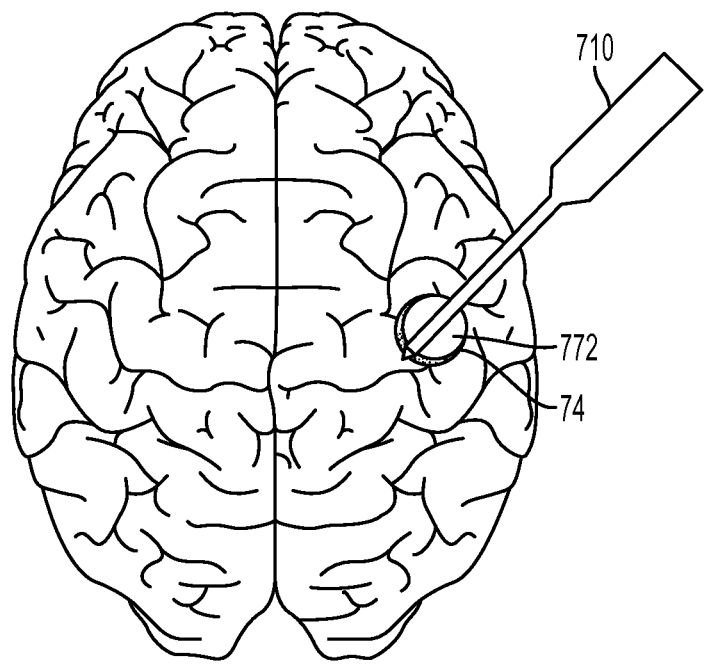
FIG. 18B is a schematic view of the device of FIG. 17B with the inflatable member inflated within the cavernous malformation.

As shown in FIGS. 18A-18B, the methods and devices disclosed herein can be used to treat a cavernous malformation, for example by delivering one or more drugs thereto. Referring to FIG. 18A, a CED device such as the device 710 described above can be inserted into a cavernous malformation 74 such that the outlet port 728A of the first fluid delivery conduit 716A and the outlet port 728B of the second fluid delivery conduit 716B are both disposed within the cavernous malformation 74. Fluid containing a drug, such as one or more antiangiogenesis factors can then be supplied to the interior of the cavernous malformation 74 through the second fluid delivery conduit 716B. At the same time, or shortly thereafter, fluid can be supplied through the first fluid delivery conduit 716A to inflate the inflatable member 772 and/or increase the pressure within the inflatable member 772, as shown in FIG. 18B. As the inflatable member 772 inflates within the cavernous malformation 74, and/or as the pressure increases within the inflatable member 772, a compressive force is exerted on the drug-containing fluid previously released into the cavernous malformation 74, pressing the fluid into the surrounding tissue.

The microfluidic CED devices disclosed herein can be manufactured using any of a variety of techniques. For example, the devices can be manufactured by micro-fabricating a silicon substrate, and then coupling the finished piece to a catheter portion that includes one or more microcapillaries. In some embodiments, a lithographic microfabrication process can be used to manufacture a CED device. The process can include (1) back etching a silicon substrate to form shank and tailpiece depths, (2) spin coating polyimide on the top side of the silicon substrate, (3) spin coating sacrificial resist to define the micro-channels, (4) applying a parylene coat to the top side of the polyimide layer, (5) applying an aluminum mask for removing the sacrificial resist and thereby forming parylene channels, and (6) front etching the silicon substrate to form device bodies. In other embodiments, the process can include (1) front etching a silicon substrate to form device bodies, (2) spray coating polyimide on both sides of the silicon substrate without masking, (3) spray coating a sacrificial resist on the polyimide, (4) applying a parylene coat to the top side, and (5) applying an aluminum mask for removing the sacrificial resist and thereby forming parylene channels.

Figure 19:
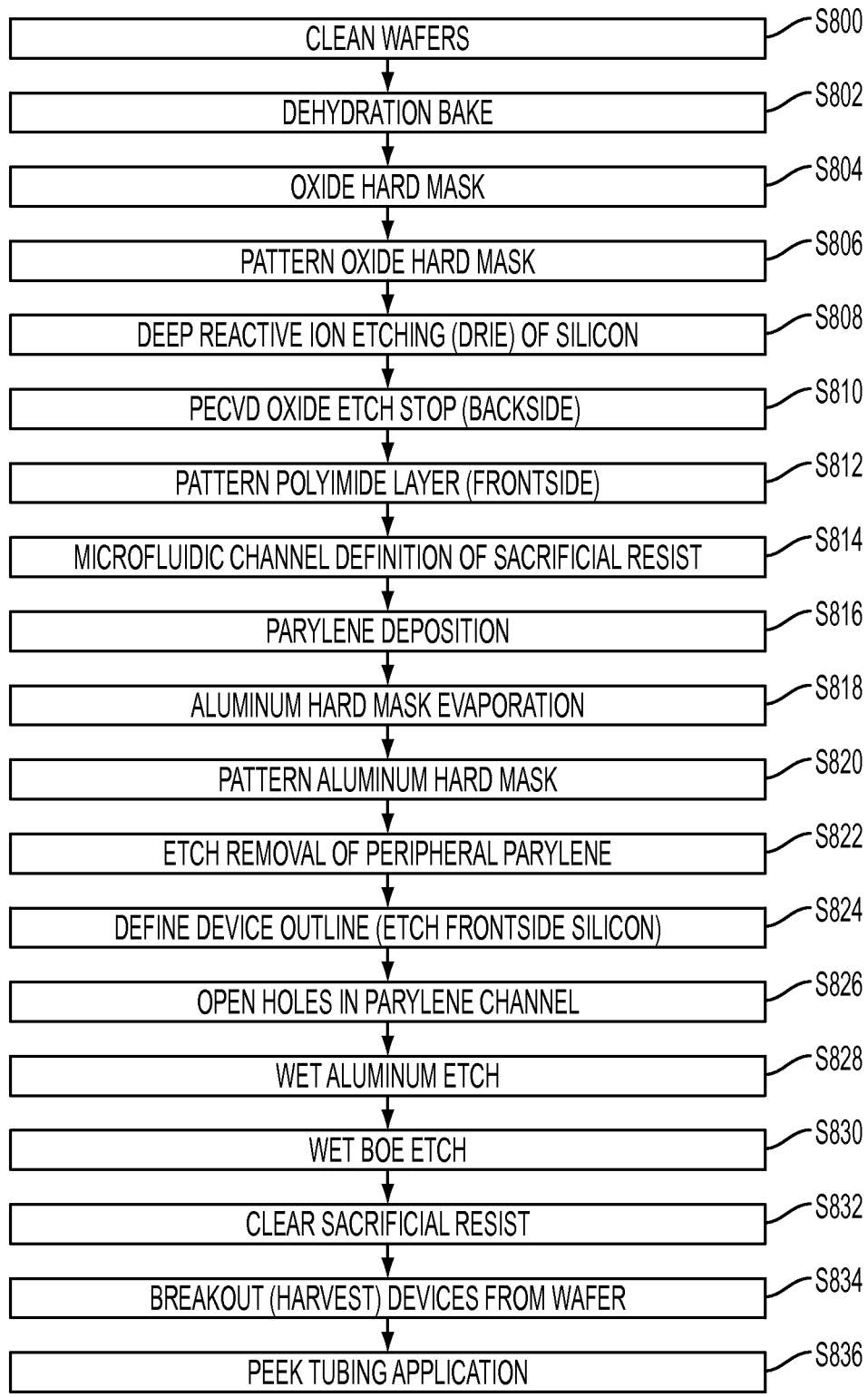
FIG. 19 is a flowchart that depicts an exemplary method of manufacturing a microfabricated CED device.

FIG. 19 illustrates an exemplary microfabrication process for manufacturing a CED device. While various methods or processes disclosed herein may be shown in relation to a flowchart or flowcharts, it should be noted that any ordering of method steps implied by such flowcharts or the description thereof is not to be construed as limiting the method to performing the steps in that order. Rather, the various steps of each of the methods disclosed herein can be performed in any of a variety of sequences. In addition, as the illustrated flowchart(s) are merely exemplary embodiments, various other methods that include additional steps or include fewer steps than illustrated are also within the scope of the present invention.

In step S800, a cleaning process can be performed on a silicon wafer from which the CED device will be fabricated. For example, a hot nanostrip clean can be performed for 30 minutes at 50 degrees C., followed by a deionized ("DI") water rinse and spin rinse drying ("SRD"), e.g., using a VERTEQ spin rinse dryer. In other embodiments, an RCA clean is performed for 15 minutes at 70 degrees C. using NH4OH:H2O, followed by 15 minutes at 70 degrees C. using HCL:H2O, followed by a DI water rinse and SRD.

In step S802, the wafer can undergo a dehydration bake. In some embodiments, the wafer can be baked at 180 degrees C. for 5 minutes using a contact hotplate. The dehydration bake can be omitted in some cases, as the wafer can be heated to 400 degrees C. during the plasma-enhanced chemical vapor deposition ("PECVD") step discussed below. Accordingly, the step time in the PECVD process can be increased to accommodate extra dehydration time. Omitting hotplate dehydration can also reduce contamination left behind by prior uses of the hotplate.

In step S804 an oxide hard mark can be deposited on the silicon wafer. In some embodiments, the hard mark can be deposited by PECVD Oxide Deposition (2.5 µm, N1.46 Oxide Recipe), and the thickness can be confirmed using a measuring system, such as those manufactured by FILMETRICS.

Figure 20A:
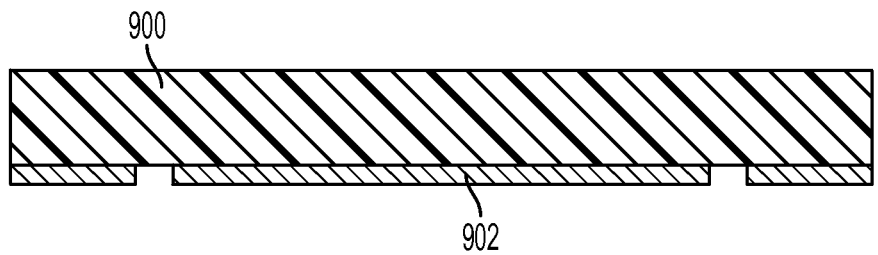
FIGS. 20A-20L are cross-sectional views of a CED device at various stages of the process of FIG. 19.

In step S806, the oxide hard mask 902 can be patterned on the silicon wafer 900, for example as shown in FIG. 20A. An exemplary patterning process includes:

Clean mask in hot strip bath (15 minutes, 70 degrees C., NMP/TMAH/PG with DI rinse and SRD.

Resist process (backside)

Vapor prime (this can be performed in an oven, such as those manufactured by YIELD ENGINEERING SYSTEMS ("YES") and can be important for the wet etch process)

Spin resist: S1813 (4000 rpm, 1000 rpm/sec, 30 sec)

Softbake: 115 degrees C.: 90 sec

Acetone swab removal of residual backside resist

Expose: MA6: Soft Contact: MASK1=DRIE (deep reactive ion-etching) (Backside)

PE Wait: None

PE Bake: 115 degrees C.: 60 sec

Develop: HAMATECH 726MIF 60 secDP

Hardbake: 115 degrees C.: 60 sec

Descum using an etcher, such as an OXFORD 80 etcher (Oxygen Plasma Clean, 150 wattsRF, 50 sccms O2, 60 mTorr, 15 sec)

Buffered Oxide Etch ("BOE") 6:1 Etch: 30 min, Extended DI Rinse and SRD

Microscope Evaluation (with Saved Images)

Oxide Etch: OXFORD 80#2 (CHF3O2 Oxide Etch, 240 watts, 100 min (×5 twenty min cycles), 50 sccms CHF3, 2 sccms O2, 40 mTorr, 10 degC, DC Bias 119 volts)

Strip Resist: OXFORD 80 (Oxygen Plasma Clean, 150 wattsRF, 50 sccms O2, 60 mTorr, 10 min)

Strip Resist: Hot Strip Bath (15 min 70 deg NMP/TMAH/PG), DI Rinse and SRD

Strip Resist: Acetone Bath, isopropyl alcohol ("IPA") Bath, DI Water Bath with DI Rinse and SRD Strip Resist, e.g., using a hot piranha cleaning system manufactured by HAMATECH Because BOE is isotropic (i.e. etches at the same rate in all directions) 30 min of BOE6:1 Etch can result in an approximately 3 µm undercut all around. This can increase the critical dimensions of the structures beyond that in the CAD layout. This can be compensated to some extent in the CAD layout (e.g., by making the dimensions smaller than what is actually desired by 3 µm).

In some embodiments, instead of using wet BOE to pattern the oxide, a CHF3O2 reactive ion "dry" etch can be used. One advantage of using BOE is that it can be relatively inexpensive (no tool charges and many wafers can be etched at the same time) and a thinner resist can be used (such as S1813). One disadvantage, however, is that the dimensions can extend out by 3 µm all around. This can be less of a concern when the critical feature sizes are really large. Another potential problem is that BOE can sometimes capillary underneath the resist layer (hence the need for good adhesion) and etch in regions where etching is not intended. For CHF3O2 reactive ion etch ("RIE"), the critical dimensions in the CAD layout can be more reliably reproduced on the wafer so there is no need to do any first-order size compensation in CAD. Also, for CHF3O2, a thicker resist (SPR220-4.5) can be required to etch through the 2.5 µm PECVD oxide hard mask.

In some embodiments, the resist can be left in place during the initial etching steps in the subsequent Bosch DRIE. Resist stripping can be done with a first O2 plasma clean followed by a wet chemical stripper followed by a DI rinse and dry N2 blow dry.

Figure 20B:
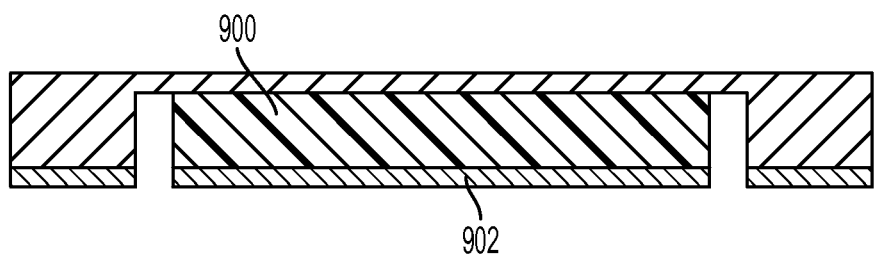

In step S808 the silicon can undergo deep reactive ion etching ("DRIE") to remove silicon from the wafer 900 in the pattern defined by the oxide hard mask 902, for example as shown in FIG. 20B. First, the edge bead is removed (if the resist was not removed previously). Then, an etching system such as those manufactured by UNAXIS can be used to etch through the wafer, leaving 100 µm remaining on the frontside. In some embodiments, the etch can be performed using the following parameters:

Chamber Season: ×100 Loops O-Trench
Wafer Etch: ~800 Loops O-Trench (400 µm into 500 µm Wafer)
Step1: Deposition
RF1 Power: 0.1 watts, Flowrate: SF6: 2 sccms, Heat Exch1: 22 degC
RF2 Power: 850 watts, Flowrate: C4F8: 60 sccms, Heat Exch2: 40 degC
Pressure: 24 mTorr, Flowrate: Ar: 40 sccms, He Flow: 2.76 sccms
Time: 4.0 sec, Flowrate: O2: 0 sccms, He Pressure: 3.0 Torr
Step2: Etch1
RF1 Power: 8.0 watts, Flowrate: SF6: 70 sccms, Heat Exch1: 22 degC
RF2 Power: 850 watts, Flowrate: C4F8: 2 sccms, Heat Exch2: 40 degC
Pressure: 23 mTorr, Flowrate: Ar: 40 sccms, He Flow: 2.76 sccms
Time: 2.0 sec, Flowrate: O2: 0 sccms, He Pressure: 3.0 Torr
Step3: Etch2
RF1 Power: 8.0 watts, Flowrate: SF6: 100 sccms, Heat Exch1: 22 degC
RF2 Power: 850 watts, Flowrate: C4F8: 2 sccms, Heat Exch2: 40 degC
Pressure: 24 mTorr, Flowrate: Ar: 40 sccms, He Flow: 2.76 sccms
Time: 6.0 sec, Flowrate: O2: 0 sccms, He Pressure: 3.0 Torr 4

Figure 20C:
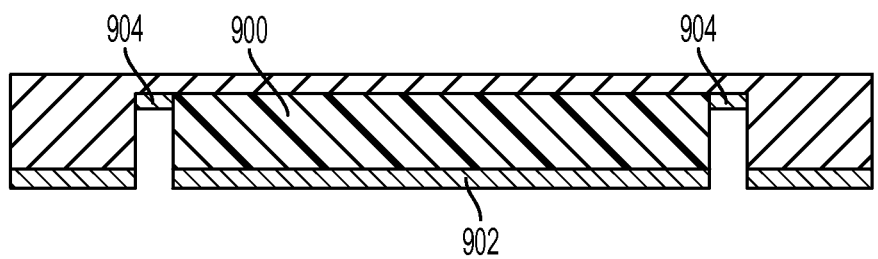

In some embodiments, an OERLIKON etching can be performed instead. Thinner wafers (e.g., about 300 µm thick as opposed to about 500 µm thick) can be used in some embodiments to reduce the etching time, however this can increase cost and breakage rate. The etching process can be followed by:

Strip Resist: OXFORD 80 (Oxygen Plasma Clean, 150 wattsRF, 50 sccms O2, 60 mTorr, 10 min)
Strip Resist: Hot Strip Bath (15 min 70 deg NMP/TMAH/PG), DI Rinse and SRD In step S810, a PECVD oxide etch stop can be performed on the backside of the wafer, for example as shown in FIG. 20C. In some embodiments, the PECVD oxide 904 can be deposited down at the very bottom of the trenches formed in step S808, e.g., using PECVD oxide deposition of 1.0 µm on the backside of the wafer with frontside etch stop. In some embodiments, a silicon on insulator ("SOI") wafer can be used, in which case the buried oxide ("BOX") layer on the SOI wafer can act as the etch stop making the PECVD stop layer and DRIE from the backside unnecessary. Vapor hydrogen fluoride ("HF") can be used in such embodiments to release the final device from the BOX.

Figure 20D:
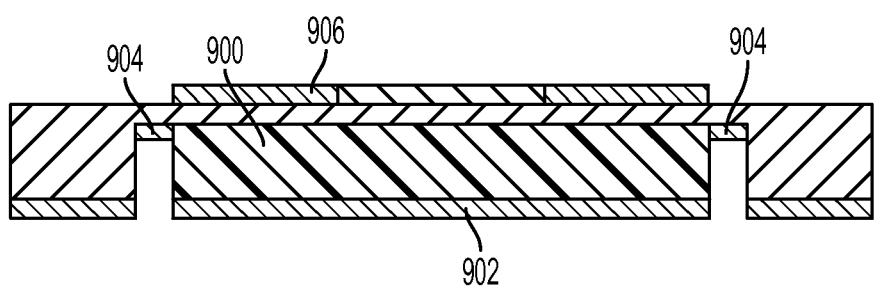
Figure 20E:
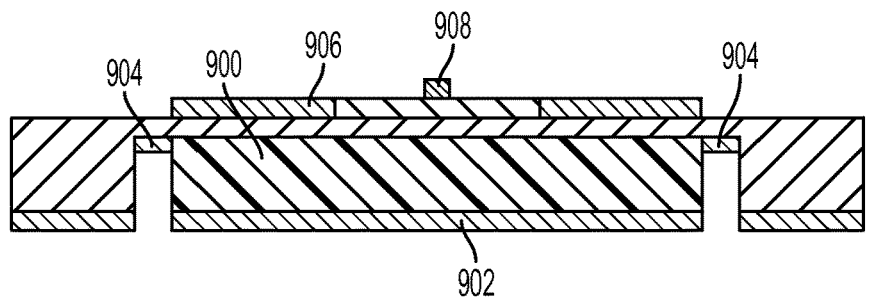

In step S812, a polyimide layer 906 can be patterned on the frontside of the wafer 900, for example as shown in FIG. 20D. In some embodiments, the following process is used to pattern the polyimide layer:

Spin polyimide (4000 rpm, 500 rpm/sec, 45 sec, ~2 µm). This can be performed using a aromatic polyimide precursor solution such as Photoneece PW DC1000 manufactured by TORAY
Clean backside residue with acetone swab
Softbake: 115 degrees C.: 3 min (contact polyimide hot plate)
Expose: MA6: Soft Contact: MASK2=POLY (Frontside)
PE Wait: None
PE Bake: None
Develop: HAMATECH 726MIF90 secDP
Microscope Evaluation (with Saved Images)
Descum: OXFORD 80 (Oxygen Plasma Clean, 150 wattsRF, 50 sccms O2, 60 mTorr, 15 sec)
Cross-Link Polyimide: Recipe3: YES Polyimide Oven: 300+ degrees C.
Typical Process: 170 degrees C. for 30 minutes and 320 degrees C. for 60 minutes in Nitrogen Ambient In step S814, the microfluidic channels can be defined using sacrificial resist 908, for example as shown in FIG. 20E. In some embodiments, the following process is used to define the microfluidic channels:

Spin Resist: SPR220-7 (1600 rpm for 10 µm, 500 rpm/sec, 45 sec)
Softbake1: 65 degrees C.: 1 min
Softbake2: 90 degrees C.: 1 min
Softbake3: 115 degrees C.: 2 min, or
Softbake: 90 degrees C., 30 min (Convection Oven)
Expose: MA6: Soft Contact: MASK3=CHANNEL (Frontside)
PE Wait: See Stanford process
PE Bake: See Stanford process
Develop: HAMATECH 726MIF120 secDP
Microscope Evaluation (with Saved Images)
Remove Edge Bead
Hardbake: 115 degrees C.: 1 min
Microscope Evaluation (with Saved Images)
Descum: OXFORD 80 (Oxygen Plasma Clean, 150 wattsRF, 50 sccms O2, 60 mTorr, 60 sec)
P10 profilometer evaluation (measure channel height and width)

The thickness of the resist layer 908 can determine the height of the microfluidic channel. Likewise, the width of the resist layer 908 (after exposure and development) determines the width of the microfluidic channel. To avoid cracking of the resist 908, this step can be done with a slow ramp up and ramp down.

In some embodiments, there can be some reflow of the resist 908 during the hardbake step which can cause it to have sloped sidewalls for better aluminum coverage. Reflow of the resist is not always necessary, however, as the wafer can also be coated using conformal evaporation or sputter deposition with both of these processes allowing many more wafers to be coated at the same time as compared to the non-conformal evaporators.

Figure 20F:
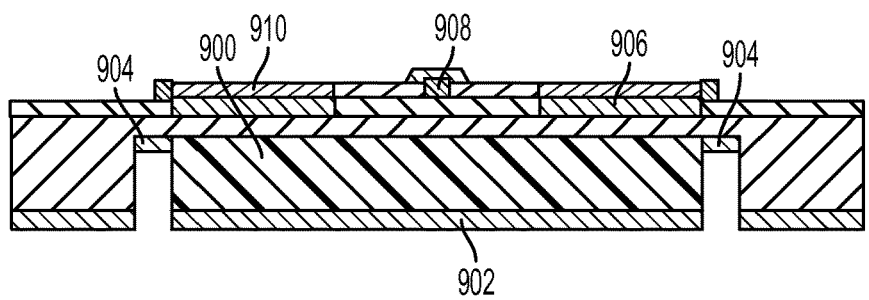
Figure 20G:
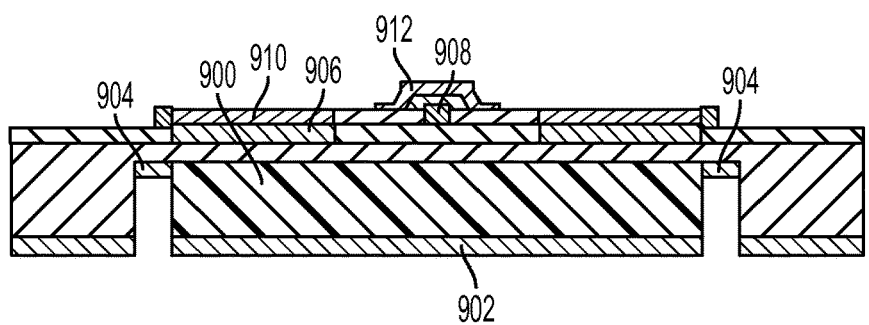

In step S816, a layer of parylene 910 is deposited over the polyimide layer 906 and the sacrificial resist 908, for example as shown in FIG. 20F. In some embodiments, the parylene layer 910 can have a thickness of approximately 5 µm. The following process can be used for the parylene deposition:

Roughen Resist Surface: OXFORD 80: 150 wattsRF, 50 sccms O2, 60 mTorr, 30 sec
Parylene C Deposition (3.5 grams=5 µm)

Parylene can be a highly conformal layer and some material can therefore be coated on the backside of each wafer. Parylene deposition can be performed on, e.g., three wafers at one time. A typical parylene deposition process can take approximately 6 hours.

In step S818, aluminum hard mask evaporation can be performed to apply an aluminum layer 912 over the parylene layer 910, as shown in FIG. 20O. The following process can be used for the aluminum hard mask evaporation:

Roughen parylene surface: OXFORD 80: 150 wattsRF, 50 sccms O2, 60 mTorr, 30 sec

Evaporate or sputter: aluminum: conformal: 150 nm (2 A/sec)

Figure 20H:
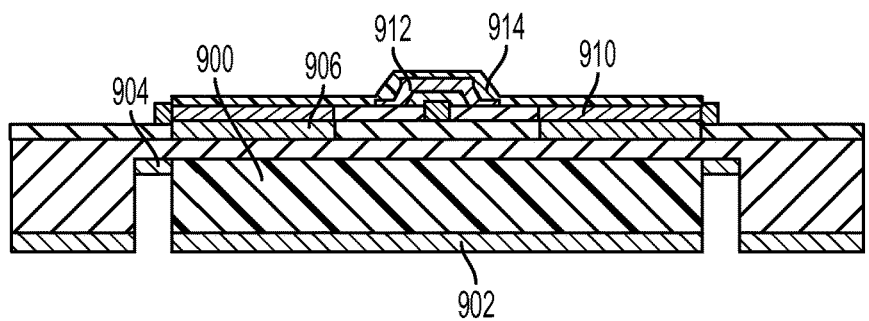

In step S820, the aluminum hard mask 912 can be patterned, for example as shown in FIG. 20H. The following process can be used to pattern the aluminum hard mask:
Liquid HMDS Prime: 10 sec
Spin Resist 914: SPR220-7 (1600 rpm, 500 rpm/sec, 45 sec, ~10 µm)
Softbake1: 65 degrees C.: 1 min
Softbake2: 90 degrees C.: 1 min
Softbake3: 115 degrees C., or,
Softbake: 90 degrees C., 30 min (Convection Oven)
Expose: MA6: Soft Contact: MASK4=ALUMINUM (Frontside)
PE Wait: None
PE Bake: None
Develop: HAMATECH 726MIF120 secDP
Microscope Evaluation (with Saved Images)
Wet Aluminum Etch (5 min)—the wet aluminum etch can undercut the resist etch mask 914 so the CAD layout can be adjusted accordingly to accommodate for this.
Microscope Evaluation (with Saved Images)
Strip Resist: OXFORD 80 (Oxygen Plasma Clean, 150 wattsRF, 50 sccms O2, 60 mTorr, 10 min)
Strip Resist: Hot Strip Bath (15 min 70 deg NMP/TMAH/PG), DI Rinse and SRD
Strip Resist: Acetone Bath, IPA Bath, DI Water Bath with DI Rinse and SRD In the above process, the chemical compatibility of the hot strip bath, acetone, and IPA with the specific polyimide chosen should be confirmed. Upon completion of step S820, a strip of aluminum 912 has been deposited overtop of the parylene layer 910 to act as a hard etch mask as per FIG. 20H.

Figure 20I:
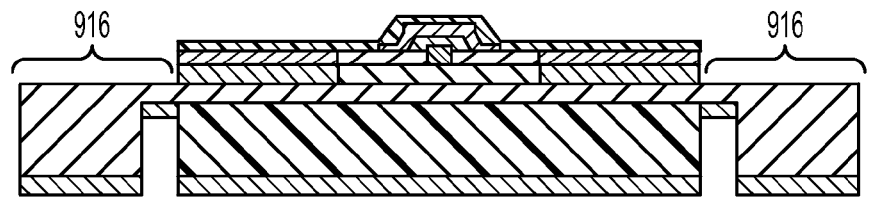

In step S822, etch removal of peripheral parylene can be performed. For example, as shown in FIG. 20I, the parylene layer 910 is removed from peripheral regions 916 of the wafer 900. The following process can be used to remove the parylene etch:
Spin Resist: SPR220-7 (1000 rpm, 100 rpm/sec, 45 sec, DynamicDispense, FreshResist, ~12 µm)
Softbake: 90 degrees C.: 30 min (Convection Oven)
Expose: MA6: Soft Contact: MASK5=PARYLENE (Frontside)
PE Wait: See Stanford process
PE Bake: See Stanford process
Develop: HAMATECH 726MIF90 secDP
Microscope Evaluation (with Saved Images)
Hardbake: 90 degrees C.: 4-12 hours (Overnight Convection Oven, Slow Ramp)
Flood UV Expose: ABM: 2 min
Parylene Etch: OXFORD 80 (Frontside, Oxygen Plasma Clean, 150 wattsRF, 20-25 min, Complete Removal of 5 µm Parylene Layer)
Parylene Etch: OXFORD 80 (Backside, Oxygen Plasma Clean, 150 wattsRF, 10-15 min with Chips)

When etching the wafer backside, silicon chips can be used to suspend the wafer above the platen so that the frontside of the wafer isn't scratched or damaged. FIG. 20I illustrates the system after parylene etch removal. As shown, the parylene has been etched all the way down to the silicon surface in the peripheral regions and 100 µm of silicon around the periphery of each device is holding the device affixed to the wafer. After the parylene etch, it can be helpful to have at least 4 µm of resist remaining that can be subsequently used for etching the remaining 100 µm of silicon on the frontside. Accordingly, the resist layer can be made thick enough to accommodate 5 µm of parylene etching and 100 µm of silicon etching. Otherwise, a new resist layer can be applied.

Figure 20J:
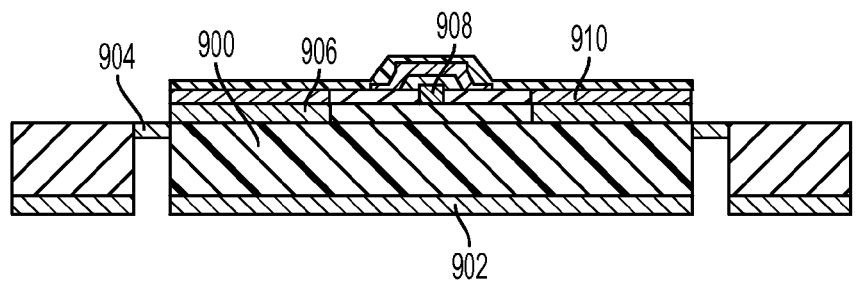
Figure 20K:
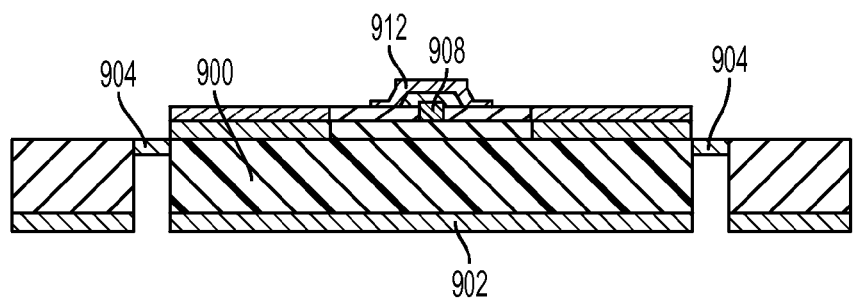
Figure 21A:
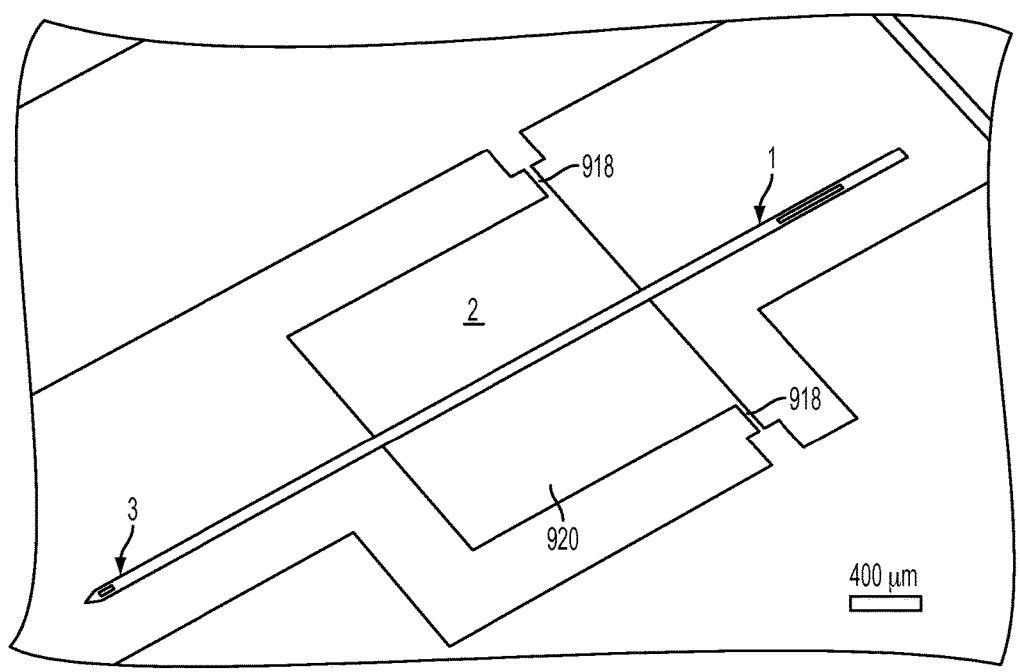
FIG. 21A is a scanning electron microscope image of a microfabricated CED device.

In step S824, the device outline can be defined, for example as shown in FIG. 20J. The following process can be used to define the device outline:
Acetone Swab Removal of Edge Bead
Softbake: 90 degrees C.: 90 min (Convection Oven)
P10 profilometer evaluation: confirm remaining resist thickness is >4 µm
UNAXIS Etch: O-Trench (to clear 100 µm of Si)
Strip Resist: 20 min Acetone Bath, 20 min IPA Bath, 20 min DI Water Bath and SRD
Strip Resist: OXFORD 80 (Oxygen Plasma Clean, 150 wattsRF, 50 sccms O2, 60 mTorr, 2 min)
Strip Resist: 20 min Acetone Bath, 20 min IPA Bath, 20 min DI Water Bath and SRD In Mask5=PARYLENE, there can be provided two small "bridges" of resist that protect the underlying parylene and that can be used to hold the device in place. Upon completion, these devices can be "broken out" from the wafer using tweezers. Preferably, these bridges can be attached to the body of the device (and not the shaft or the shoulder). Exemplary bridges 918 are shown in FIG. 21A, at the proximal end of the device body 920. As shown in FIG. 20K, after the resist strip, one can "see" through the PECVD oxide membrane layer 904 that tethers around the periphery of each device.

In step S826, holes can be opened in the parylene channel(s). In this step, the aluminum 912 can be used as a hard mask to open up access holes into the parylene channel. Over-etching can be preferred here to make sure that the parylene 910 has been cleared and the sacrificial resist 908 is accessible. Prior to this step, there is no access by any solvents to the sacrificial resist 908 inside the channel. The following process can be used to open holes in the parylene channel:
Parylene Etch: OXFORD 80: Oxygen Plasma Clean: 150 wattsRF, 50 sccms O2, 60 mTorr, 20-25 min Etch)
Microscope Evaluation (with Saved Images)

In step S828, a wet aluminum etch can be performed to remove the etch mask, for example using the following process:
Wet Aluminum Etch, 15 min, DI Rinse and SRD
Microscope Evaluation (with Saved Images)

In step S830, a wet BOE etch can be performed to remove the PECVD oxide stop layer 904, for example using the following process:
BOE6:1 Etch, 10-15 min In some embodiments, after the BOE etch, each device is held in place only by the device "tabs" or "bridges" in the 1 µm silicon layer.

Figure 20L:
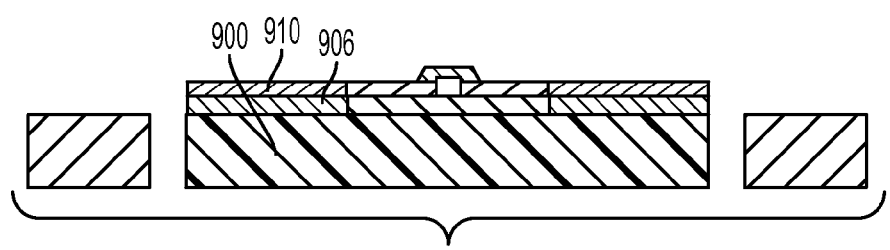

In step S832, the sacrificial resist 908 can be cleared, for example as shown in FIG. 20L. The following process can be used to clear the sacrificial resist:
Clear Resist: Acetone Bath: 4 hrs (Keep Wet)
Clear Resist: IPA Bath: 1 hr (Keep Wet)
Clear Resist: DI Water Bath: 12 hrs In some embodiments, the wafers are not allowed to dry in-between these bathing steps, which can prevent resist residue from crystallizing at the inlet/outlet ports. After sacrificial resist removal, the device cross section is as shown in FIG. 20L. In some embodiments, the sacrificial resist is removed before the individual devices are harvested (i.e., broken-out) from the wafer, making the resist removal process less cumbersome and time-consuming.

In step S834, the devices can be harvested from the wafer. This can be performed, e.g., by using tweezers to push on the body of each device until the tabs break and the device falls from the wafer onto a clean wipe. Once separated from the wafer, the device can be picked up from the clean wipe and placed into a tacky GelBox, preferably with the access ports facing up.

In step S836, the devices can be assembled with PEEK tubing to form a finished CED device. The contact surface of the PEEK tubing can be treated using O2 plasma and mechanical roughening for good adhesion, and then attached to the device using an adhesive such as Epoxy 907 manufactured by MILLER-STEPHENSON.

In an exemplary embodiment, the finished devices can have an 1850 μm catheter tip length, a 1750 μm square body, a 1750 μm shoulder length, and a nominal catheter tip width of 25 μm. Leaving allowance for test areas around the periphery, 100 or more of such devices can be fabricated from a single 4-inch wafer.

Figure 21B:
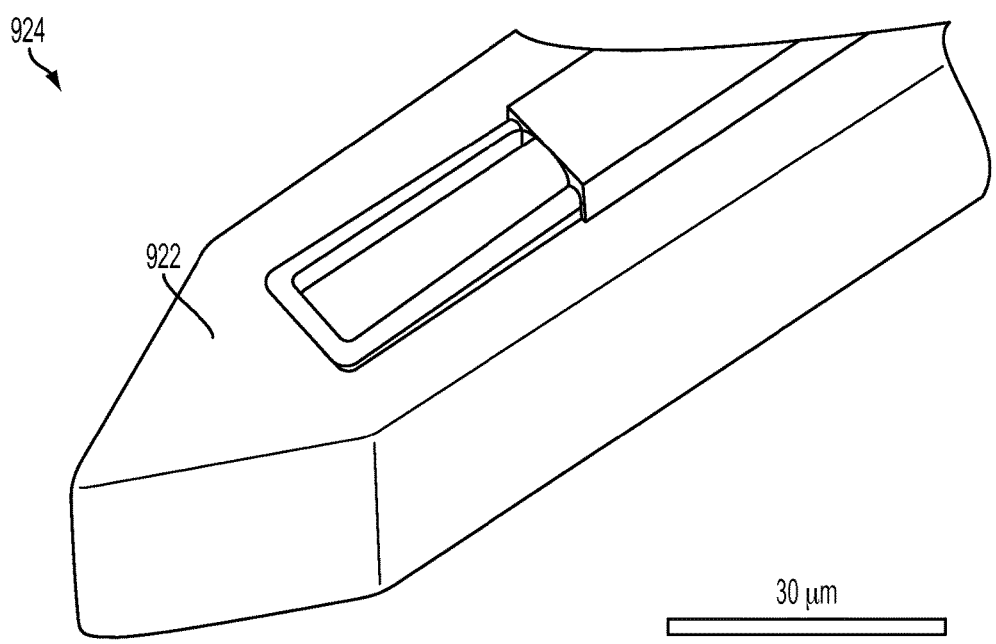
FIG. 21B is a scanning electron microscope image of the distal tip of the CED device of FIG. 21A.

FIG. 21B illustrates a scanning electron microscope (SEM) image of the tip 922 of a completed CED device 924. The sidewall roughness shown in the image, which can undesirably result in crack propagation, can be reduced by incorporating a wet flash etch of the silicon into the above process.

Figure 22A:
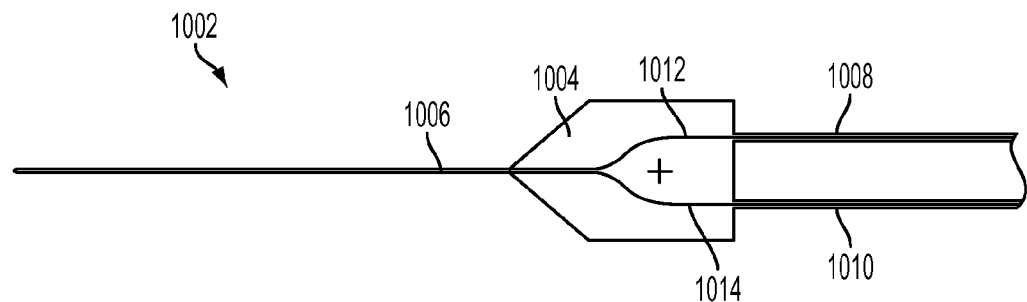
FIG. 22A is a schematic top view of a microfabricated CED device.
Figure 22B:
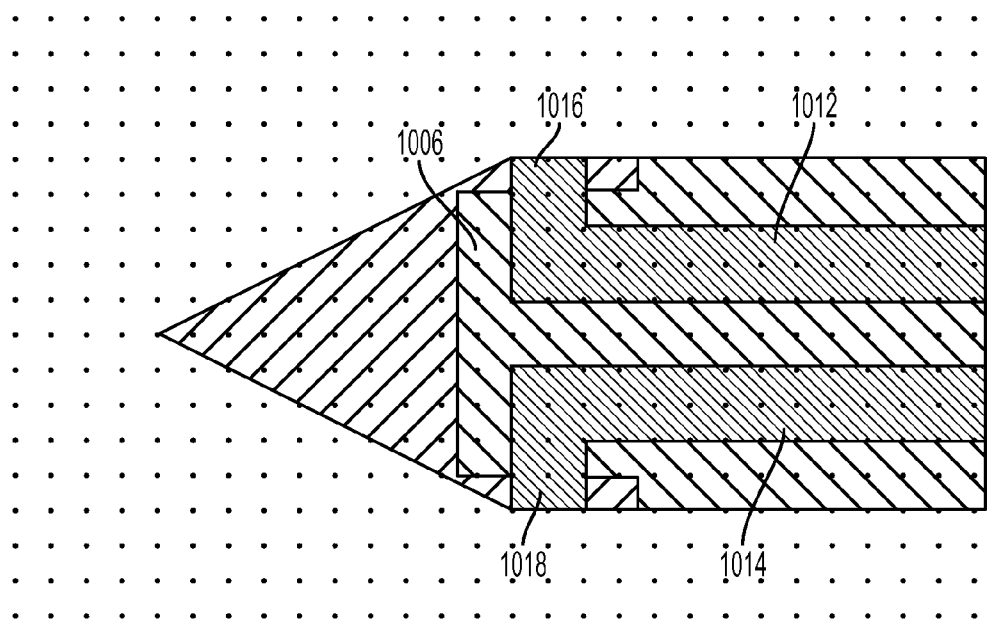
FIG. 22B is a detail schematic top view of the distal tip of the CED device of FIG. 22A.

The microfabricated portion 1002 of a multi-lumen CED device 1000 (manufactured, for example, using the above process) is illustrated schematically in FIG. 22A. As shown, the microfabricated portion 1002 includes a body portion 1004 with a shank or tip 1006 extending distally therefrom and first and second legs 1008, 1010 extending proximally therefrom. In exemplary embodiments, the body portion can have a length of approximately 1.5 mm. First and second parylene channels 1012, 1014 are formed on the silicon substrate. The first parylene channel 1012 extends along the first leg 1008, across the body portion 1004, and along the tip 1006. The second parylene channel 1014 extends along the second leg 1010, across the body portion 1004, and along the tip 1006. As shown in FIG. 22B, the parylene channels 1012, 1014 can include 90 degree turns at their distal end, such that the outlet ports 1016, 1018 of the channels are aimed in a direction perpendicular to the longitudinal axis of the tip 1006.

Figure 23A:
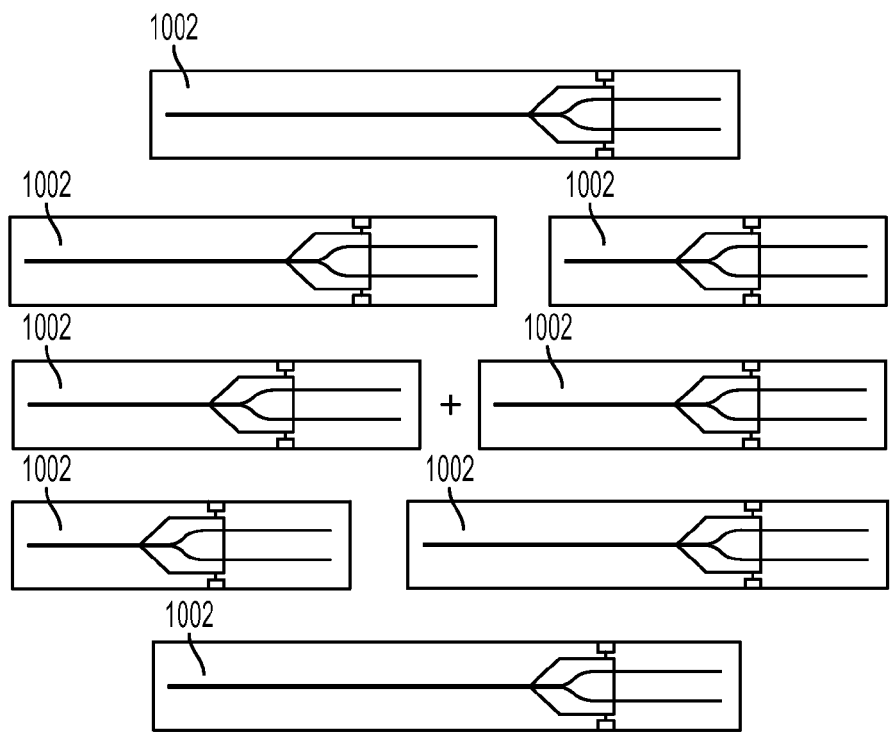
FIG. 23A is a schematic view of a wafer layout that includes a plurality of microfabricated CED devices.
Figure 23B:
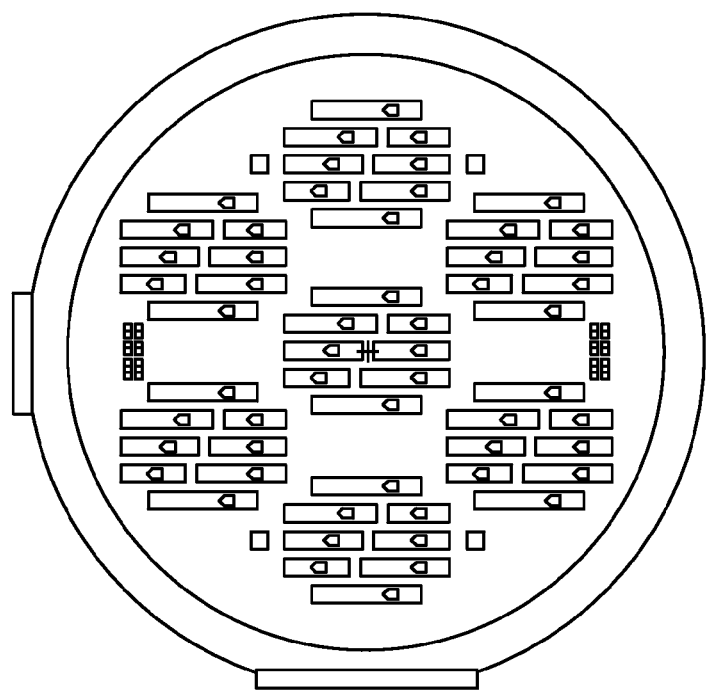
FIG. 23B is a schematic view of the wafer layout of FIG. 23A repeated a plurality of times on a silicon wafer.
Figure 23C:
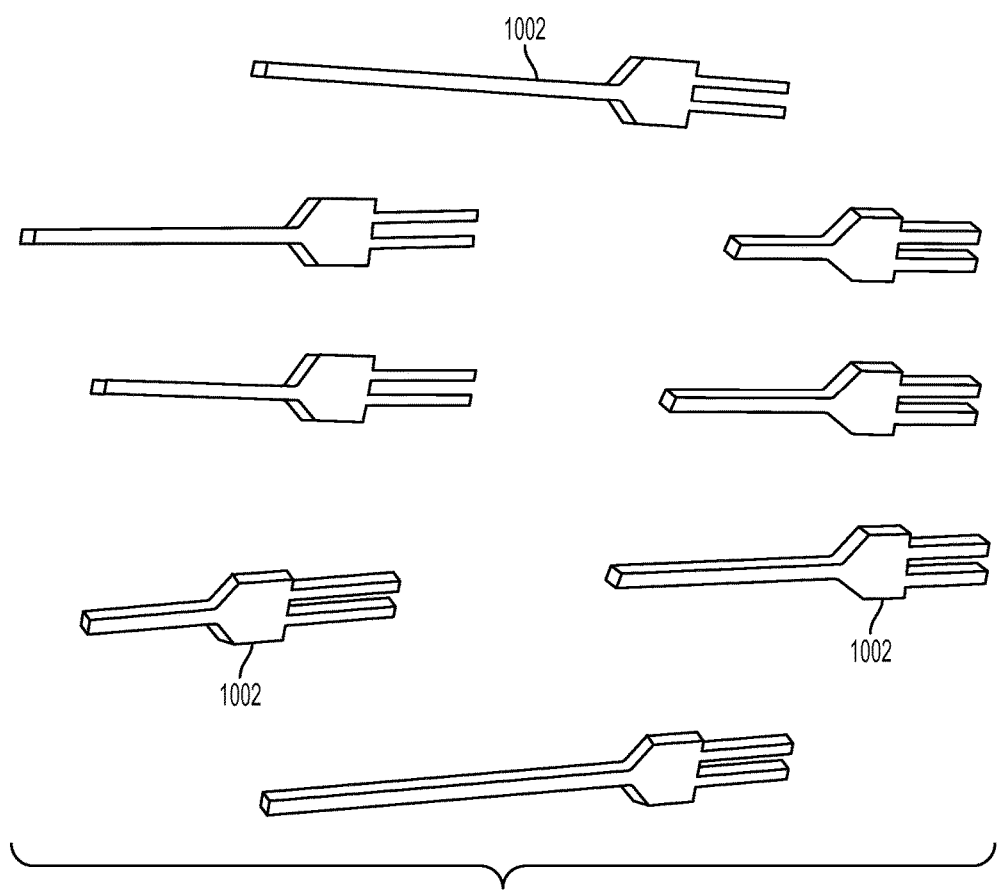
FIG. 23C is an image of a plurality of microfabricated CED devices produced using the layout of FIG. 23A.

FIG. 23A illustrates a layout of eight microfabricated portions 1002 having various lengths. As shown in FIG. 23B, the layout of FIG. 23A can be repeated across the available surface area of a silicon wafer. FIG. 23C illustrates a set of eight microfabricated portions 1002 after having been harvested from the wafer.

Figure 24A:
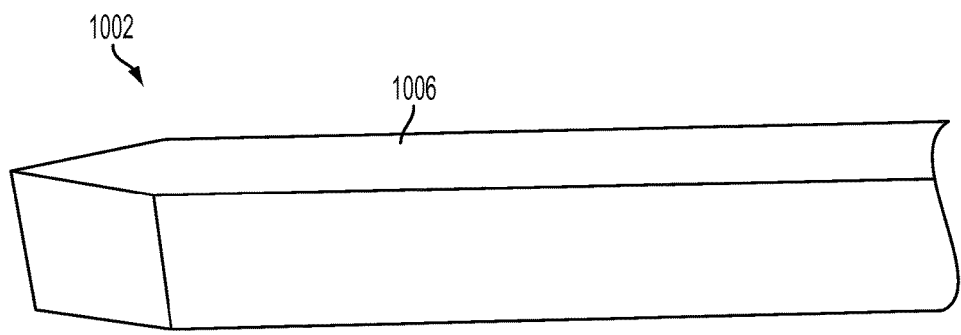
FIG. 24A is a microscope image of a silicon substrate formed during manufacture of a CED device.
Figure 24B:
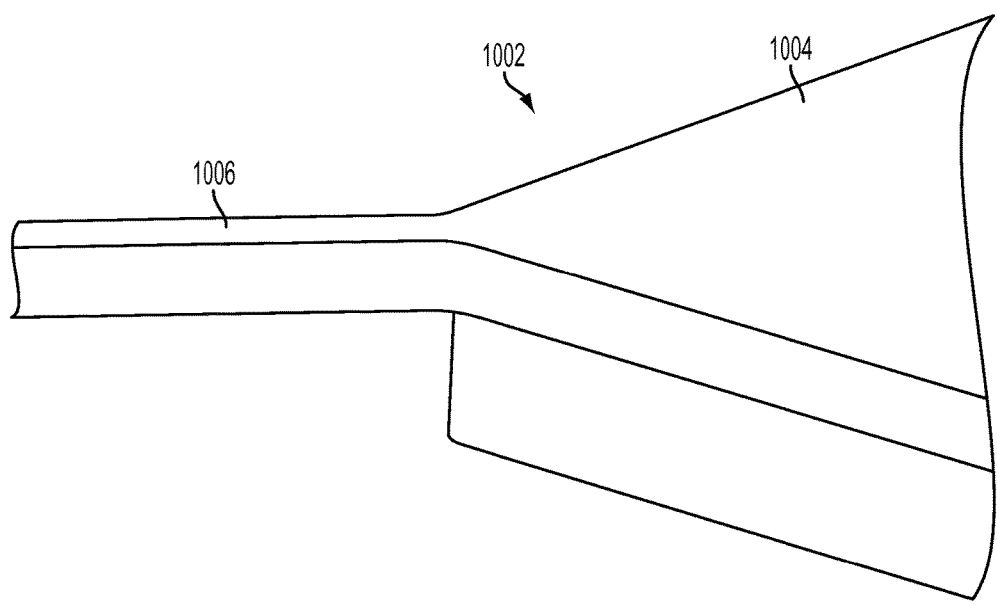
FIG. 24B is another microscope image of the substrate of FIG. 24A.
Figure 24C:
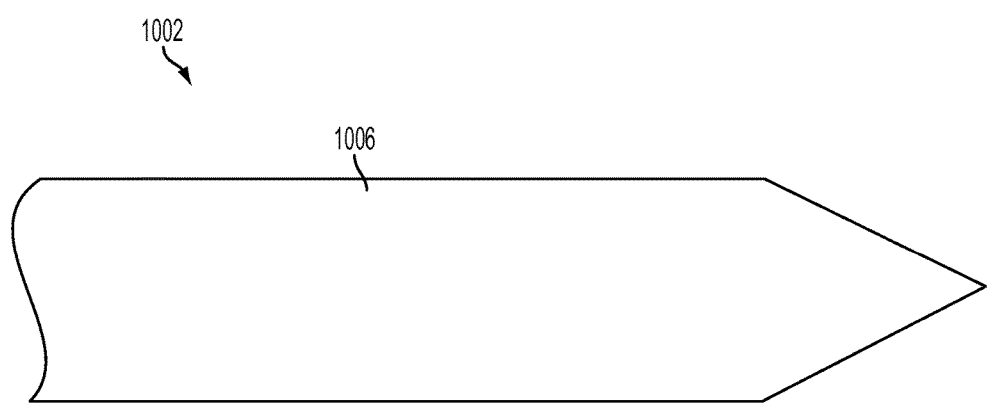
FIG. 24C is another microscope image of the substrate of FIG. 24A.

FIGS. 24A-24C illustrate SEM images of the microfabricated portions 1002 of the device 1000, before creation of the parylene channels 1012, 1014.

Figure 25A:
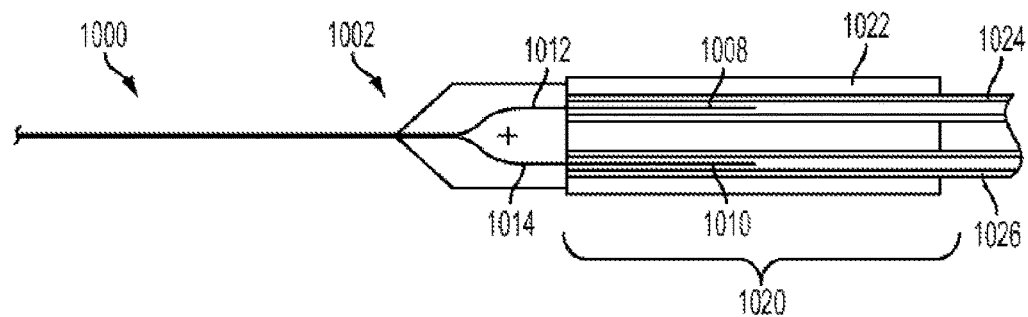
FIG. 25A is a schematic top view of a microfabricated CED device having an attached catheter portion.

As shown in FIG. 25A, the multi-lumen CED device 1000 also includes a proximal catheter portion 1020 which can be assembled with the microfabricated portion 1002. The catheter portion 1020 can include a quartz double-bore body 1022 with first and second PEEK micro-capillaries 1024, 1026 extending therethrough. The catheter portion 1020 can be mated to the microfabricated portion 1002 by inserting the first and second legs 1008, 1010 into the body 1022, such that the first and second micro-capillaries 1024, 1026 are in fluid communication with the first and second parylene channels 1012, 1014. An adhesive can be used as described above to couple the two portions 1002, 1020 of the device 1000 to one another and to form a fluid-tight seal.

Figure 25B:
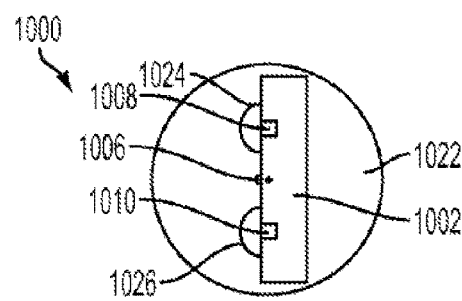
FIG. 25B is a schematic end view of the device of FIG. 25A.
Figure 25C:
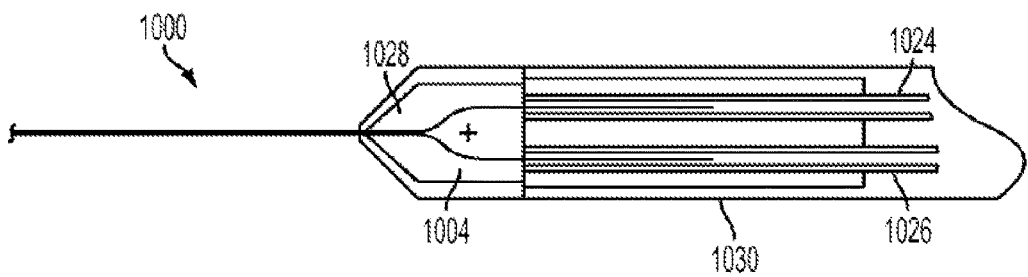
FIG. 25C is a schematic top view of the device of FIG. 25A with a nose portion and catheter body coupled thereto.
Figure 25D:
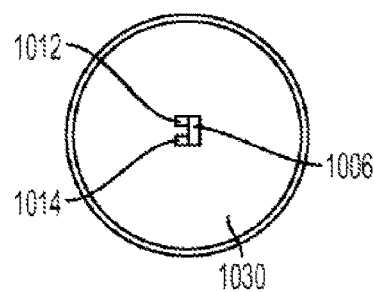
FIG. 25D is a schematic end view of the device of FIG. 25C.
Figure 26A:
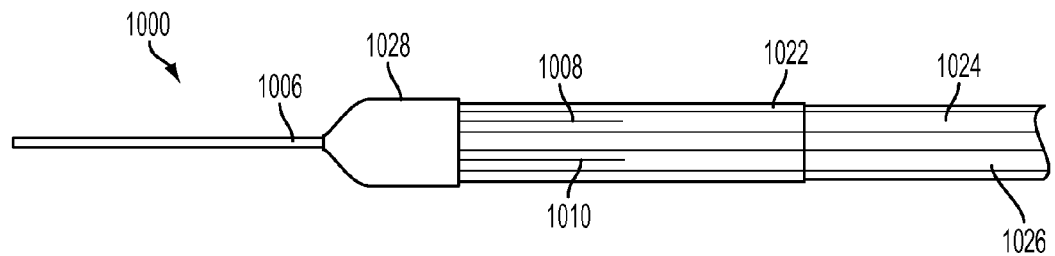
FIG. 26A is a top view image of an assembled CED device.
Figure 26B:
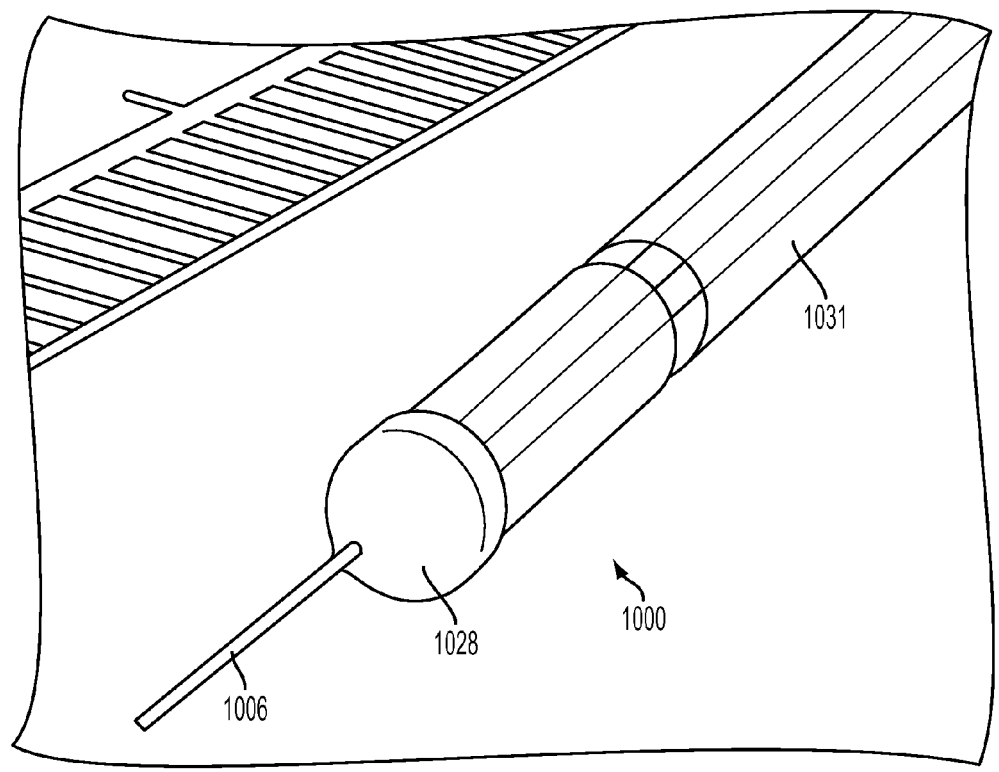
FIG. 26B is a perspective view image of the CED device of FIG. 26A.
Figure 26C:
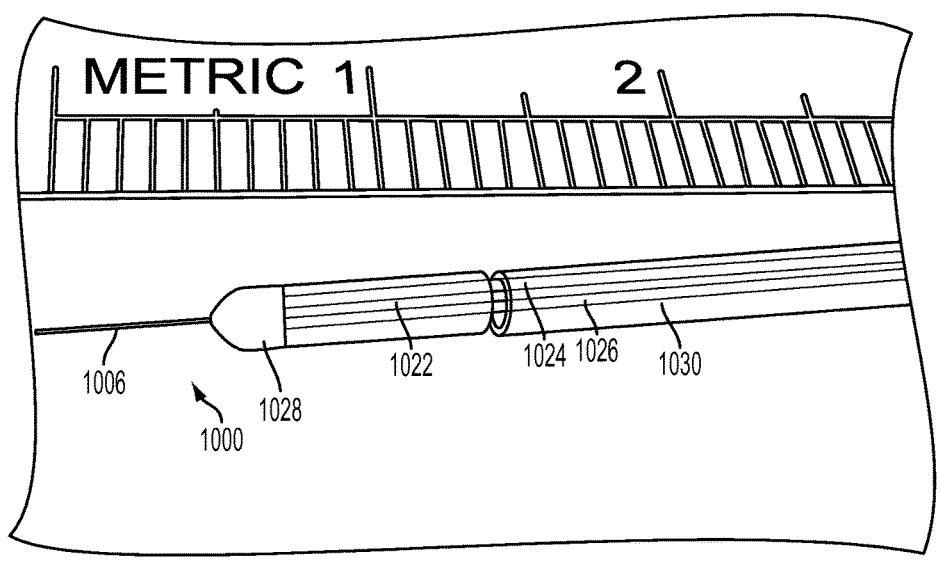
FIG. 26C is a top view image of the CED device of FIG. 26A shown with a reference scale.

A proximal end-view of the device 1000 at this stage of assembly is shown in FIG. 25B. As shown, the silicon body portion 1004 extending from the catheter portion 1020 has a flat, generally rectangular shape, which if left exposed can make tissue penetration with the device 1000 difficult. As shown in FIG. 25C, a nose portion 1028 can be coupled to the device 1000 to encapsulate the flat wafer body 1004. The nose portion 1028 can have any of a variety of shapes, including conical, cylindrical, hemispherical, and so forth, and can be sharp or blunt. The gradual taper provided by the nose portion 1028 can facilitate insertion of the device 1000 into tissue and can also form a better seal with surrounding tissue, thereby reducing the possibility for fluid delivered under pressure through the device 1000 to migrate back along the exterior surface of the device away from the target treatment area. In exemplary embodiments, the nose portion 1028 has a maximum outside diameter of between about 1 mm and about 1.5 mm. The nose portion 1028 can be formed using epoxy or it can be a separate micro-machined part that is assembled onto the microfabricated portion 1002. As also shown in FIG. 25C, a catheter/cannula body 1030 can extend over the catheter portion 1020 of the device 1000 to encapsulate the proximal end of the microfabricated portion 1002 and the micro-capillaries 1024, 1026. A proximal end view of the device 1000 at this stage of assembly is shown in FIG. 25D. Images of an exemplary assembled device are shown in FIGS. 26A-26C.

In some embodiments, the device 1000 can be configured to deliver fluid at a flow rate between about 5 μL per minute and about 10 μL per minute. To achieve such flow rates, the channels 1012, 1014 can each have a height of approximately 10 microns and a width of approximately 20 microns in the case of a rectangular channel, or can each have a diameter of about 20 microns in the case of a round channel.

Any of the various treatments described herein can further include delivering a cofactor to the target tissue, such as a corticosteroid impregnated in the scaffold of the device, a corticosteroid coated onto the scaffold, and/or a propagation enhancing enzyme. In addition, any of the various treatments described herein can further include long-term implantation of the device (e.g., for several hours or days) to facilitate long-term treatments and therapies.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A microfluidic convection-enhanced-delivery (CED) device, comprising:
   a shank portion;
   at least one fluid delivery conduit having a proximal end, a distal end, a fluid inlet port, and at least one fluid outlet port, the at least one fluid delivery conduit being formed in or on the shank portion, the at least one fluid delivery conduit comprising first and second upstream lumens and a single downstream lumen;
   a flow restriction formed within the at least one fluid delivery conduit at a merge of the first and second upstream lumens into the single downstream lumen, the flow restriction being configured to adjust a pressure of fluid being directed through the at least one fluid delivery conduit;
   wherein the flow restriction comprises a constricted region of the at least one fluid delivery conduit having a cross-sectional area that is less than a cross-sectional area of a proximally-adjacent portion of the at least one fluid delivery conduit;

wherein the at least one fluid outlet port includes a plurality of fluid outlet ports formed in the first and second upstream lumens and a plurality of fluid outlet ports formed in the single downstream lumen; and wherein the plurality of fluid outlet ports formed in the first and second upstream lumens are formed in an outermost surface of the microfluidic CED device and disposed such that fluid exits from the first and second upstream lumens directly to a location exterior to the microfluidic CED device.

2. The device of claim 1, further comprising an insertion support scaffold to which the shank portion is coupled.

3. The device of claim 1, wherein the shank portion is formed from silicon and the at least one fluid delivery conduit is formed from parylene.

4. The device of claim 1, wherein the cross-sectional area of the constricted region is at least about 20% less than the cross-sectional area of the proximally-adjacent portion.

5. The device of claim 1, wherein the cross-sectional area of the constricted region is at least about 30% less than the cross-sectional area of the proximally-adjacent portion.

6. The device of claim 1, wherein the cross-sectional area of the constricted region is at least about 40% less than the cross-sectional area of the proximally-adjacent portion.

7. The device of claim 1, wherein the proximally-adjacent portion has a height between about 1 micron and about 50 microns and the constricted region has a height between about 1 micron and about 25 microns.

8. The device of claim 1, wherein the proximally-adjacent portion has a width between about 10 microns and about 100 microns and the constricted region has a width between about 5 microns and about 50 microns.

9. The device of claim 1, wherein the at least one fluid outlet port comprises a wherein the plurality of fluid outlet ports are spaced a distance apart from one another between the proximal and distal ends of the at least one fluid delivery conduit.

10. The device of claim 9, wherein each fluid outlet port of the plurality of fluid outlet ports has an area that is great than an area of any of the plurality of fluid outlet ports positioned proximally thereto.

11. The device of claim 1, wherein the at least one fluid delivery conduit is formed from at least one of a parylene composition, a silastic composition, a polyurethane composition, and a PTFE composition.

12. The device of claim 1, further comprising a fluid reservoir in fluid communication with the fluid inlet port of the at least one fluid delivery conduit and configured to supply a fluid thereto under positive pressure.

13. The device of claim 1, wherein the at least one fluid delivery conduit comprises an embedded microsensor.

14. The device of claim 13, wherein the embedded microsensor comprises at least one of an interrogatable sensor, a pressure sensor, a glutamate sensor, a pH sensor, a temperature sensor, an ion concentration sensor, a carbon dioxide sensor, an oxygen sensor, and a lactate sensor.

15. The device of claim 1, wherein the at least one fluid delivery conduit is configured to aspirate fluids.

* * * * *